(12) United States Patent
Niver et al.

(10) Patent No.: US 12,295,625 B2
(45) Date of Patent: May 13, 2025

(54) APPARATUS AND METHODS FOR JOINING BONES

(71) Applicant: Medline Industries, LP, Northfield, IL (US)

(72) Inventors: Ryan Niver, Glenview, IL (US); Dinesh Koka, Winter Park, FL (US); Samuel Nader, Arlington Heights, IL (US)

(73) Assignee: Medline Industries, LP, Northfield, IL (US)

( * ) Notice: Subject to any disclaimer, the term of this patent is extended or adjusted under 35 U.S.C. 154(b) by 826 days.

(21) Appl. No.: 17/407,168

(22) Filed: Aug. 19, 2021

(65) Prior Publication Data
US 2023/0057743 A1    Feb. 23, 2023

(51) Int. Cl.
*A61B 17/80* (2006.01)
*A61B 17/68* (2006.01)

(52) U.S. Cl.
CPC ...... *A61B 17/8014* (2013.01); *A61B 17/8061* (2013.01); *A61B 17/809* (2013.01); *A61B 2017/681* (2013.01)

(58) Field of Classification Search
CPC . A61B 17/808; A61B 17/8085; A61B 17/809; A61B 17/8095; A61B 2017/0488; A61B 17/7076; A61B 17/0682; A61B 17/128
See application file for complete search history.

(56) References Cited

U.S. PATENT DOCUMENTS

| | | | |
|---|---|---|---|
| 294,777 | A | 3/1884 | Forbes |
| 324,126 | A | 8/1885 | Gay |
| D28,350 | S | 3/1898 | Reuter |
| D29,472 | S | 10/1898 | Hughes et al. |
| 1,257,807 | A | 2/1918 | Carrell |
| 1,354,737 | A | 10/1920 | Frisk |
| 1,639,530 | A | 8/1927 | Payson |

(Continued)

FOREIGN PATENT DOCUMENTS

| | | |
|---|---|---|
| EP | 0127994 | 12/1984 |
| FR | 2628312 | 9/1989 |

(Continued)

OTHER PUBLICATIONS

Stryker, EasyClip Osteosynthesis Compression Staples brochure, bearing a copyright date of 2015.

(Continued)

*Primary Examiner* — Anu Ramana
(74) *Attorney, Agent, or Firm* — Fitch, Even, Tabin & Flannery LLP

(57) ABSTRACT

Apparatus and methods are provided for using a plate to fuse bones together, including reducing or stabilizing a fracture or osteotomy. Legs of the plate are inserted into pre-drilled guide holes in one of the bones and one or more screws are inserted through apertures and into another of the bones to secure the plate to the bones. A plate insertion tool can be used to temporarily tension the legs prior to insertion into predrilled guide holes in a bone by bending or pivoting the legs away from the body. A tensioning tool can be used to tension the plate after the legs are inserted into the guide holes in the bone and during the insertion of one or more of the screws.

19 Claims, 38 Drawing Sheets

(56) References Cited

U.S. PATENT DOCUMENTS

| | | |
|---|---|---|
| 2,067,359 A | 1/1937 | Tumminello |
| 2,174,708 A | 10/1939 | Sears |
| 3,154,999 A | 11/1964 | Stewart |
| 3,316,794 A | 5/1967 | Dixon |
| 3,564,663 A | 2/1971 | Roberts |
| 3,584,347 A | 6/1971 | Klenz |
| 3,787,608 A | 1/1974 | Colby |
| 3,821,919 A | 7/1974 | Knohl |
| 3,824,995 A | 7/1974 | Getscher |
| 3,940,844 A | 3/1976 | Colby |
| 3,960,147 A * | 6/1976 | Murray ............... A61B 17/8872 606/101 |
| D243,365 S | 2/1977 | Cross |
| 4,263,903 A | 4/1981 | Griggs |
| 4,454,875 A | 6/1984 | Pratt |
| D281,814 S | 12/1985 | Pratt |
| 4,565,193 A | 1/1986 | Streli |
| 4,570,623 A | 2/1986 | Ellison |
| 4,592,346 A | 6/1986 | Jurgutis |
| D286,442 S | 10/1986 | Korthoff |
| 4,799,481 A | 1/1989 | Transue |
| 4,848,328 A | 7/1989 | Laboureau |
| 5,179,964 A | 1/1993 | Cook |
| 5,263,973 A | 11/1993 | Cook |
| 5,449,359 A | 9/1995 | Groiso |
| 5,454,814 A | 10/1995 | Comte |
| 5,662,655 A | 9/1997 | Laboureau |
| 5,674,222 A | 10/1997 | Berger |
| 5,785,713 A | 7/1998 | Jobe |
| 5,853,414 A | 12/1998 | Groiso |
| 5,941,890 A | 8/1999 | Voegele |
| 6,001,110 A | 12/1999 | Adams |
| 6,120,511 A | 9/2000 | Chan |
| 6,187,009 B1 | 2/2001 | Herzog |
| 6,325,805 B1 | 12/2001 | Ogilvie |
| 6,336,928 B1 | 1/2002 | Guerin |
| 6,401,306 B1 | 6/2002 | Hanten |
| 6,652,592 B1 | 11/2003 | Grooms |
| 6,767,356 B2 | 7/2004 | Kanner |
| 6,773,437 B2 | 8/2004 | Ogilvie |
| 7,108,697 B2 | 9/2006 | Mingozzi |
| D572,363 S | 7/2008 | Menn |
| D587,370 S | 2/2009 | Coillard-Lavirotte |
| D596,294 S | 7/2009 | Coillard-Lavirotte |
| 7,722,610 B2 | 5/2010 | Viola |
| 7,794,475 B2 | 9/2010 | Hess |
| 7,824,426 B2 | 11/2010 | Racenet |
| 8,021,389 B2 | 9/2011 | Molz, IV |
| 8,360,297 B2 | 1/2013 | Shelton, IV |
| 8,366,748 B2 | 2/2013 | Kleiner |
| 8,393,517 B2 * | 3/2013 | Milo ................. A61B 17/0644 227/181.1 |
| 8,584,853 B2 | 11/2013 | Knight |
| 8,596,514 B2 | 12/2013 | Miller |
| 8,679,154 B2 | 3/2014 | Smith |
| D705,930 S | 5/2014 | Cheney |
| 8,720,766 B2 | 5/2014 | Hess |
| D707,357 S | 6/2014 | Cheney |
| 8,808,325 B2 | 8/2014 | Hess |
| D728,103 S | 4/2015 | Katchis |
| 9,039,737 B2 | 5/2015 | Vold |
| 9,198,769 B2 * | 12/2015 | Perrow ................ A61B 17/861 |
| 9,254,180 B2 | 2/2016 | Huitema |
| 9,295,463 B2 | 3/2016 | Viola |
| 9,339,268 B2 | 5/2016 | Fox |
| 9,402,624 B1 | 8/2016 | Scott |
| 9,433,452 B2 | 9/2016 | Weiner |
| 9,463,260 B2 | 10/2016 | Stopek |
| 9,486,212 B2 | 11/2016 | Miller |
| D780,311 S | 2/2017 | Cheney |
| 9,743,926 B2 | 8/2017 | Fox |
| 9,855,036 B2 | 1/2018 | Palmer |
| 9,901,338 B2 | 2/2018 | Anderson |
| D826,405 S | 8/2018 | Shelton, IV |
| 10,058,366 B2 | 8/2018 | Bouduban |
| 10,064,619 B2 * | 9/2018 | Palmer ................ A61B 17/068 |
| 10,064,623 B2 | 9/2018 | Soutorine |
| 10,085,743 B2 | 10/2018 | Roedl |
| 10,105,134 B2 * | 10/2018 | Biedermann ....... A61B 17/0682 |
| 10,117,647 B2 | 11/2018 | Cheney |
| 10,130,358 B2 * | 11/2018 | Palmer ................ A61B 17/808 |
| 10,166,022 B2 | 1/2019 | Early |
| D840,035 S | 2/2019 | Weiner |
| 10,238,382 B2 | 3/2019 | Terrill |
| 10,307,156 B1 | 6/2019 | Blair |
| D857,199 S | 8/2019 | Cheney |
| 10,610,218 B2 | 4/2020 | Palmer et al. |
| D886,299 S | 6/2020 | Cundiff |
| D895,113 S | 9/2020 | Blair |
| 10,779,816 B2 | 9/2020 | Goldstein |
| 10,820,902 B2 | 11/2020 | Cheney |
| 10,874,389 B2 | 12/2020 | Biedermann |
| 10,918,484 B2 | 2/2021 | Ellington et al. |
| 10,945,725 B2 * | 3/2021 | Hollis ................ A61B 17/0642 |
| 10,987,101 B2 | 4/2021 | Ducharme |
| 11,000,323 B2 | 5/2021 | Stamp |
| 11,006,949 B2 | 5/2021 | Daniel |
| 11,020,110 B1 | 6/2021 | Blair |
| 11,090,043 B2 | 8/2021 | Biedermann |
| 11,116,499 B1 | 9/2021 | Blair |
| 11,278,278 B2 | 3/2022 | Biedermann |
| 11,284,886 B2 | 3/2022 | Hartdegen |
| D957,636 S | 7/2022 | Blair |
| 11,553,952 B2 * | 1/2023 | Hammann ......... A61B 17/8042 |
| 11,596,398 B2 * | 3/2023 | Wahl ................. A61B 17/0682 |
| 11,642,124 B2 | 5/2023 | Maclure et al. |
| 11,653,913 B2 | 5/2023 | Goldstein et al. |
| 11,684,359 B2 | 6/2023 | Biedermann |
| 11,911,036 B2 * | 2/2024 | Reed ................. A61B 17/0642 |
| D1,017,038 S | 3/2024 | Bushko |
| 11,937,819 B2 * | 3/2024 | Pheil ..................... A61B 17/10 |
| 2003/0225423 A1 | 12/2003 | Huitema |
| 2004/0193188 A1 | 9/2004 | Francese |
| 2005/0021035 A1 | 1/2005 | Groiso |
| 2005/0288707 A1 * | 12/2005 | De Canniere ........ A61B 17/064 606/219 |
| 2006/0058802 A1 | 3/2006 | Kofoed |
| 2007/0233113 A1 | 10/2007 | Kaelblein |
| 2007/0270906 A1 | 11/2007 | Molz |
| 2007/0276388 A1 | 11/2007 | Robertson |
| 2008/0147068 A1 | 6/2008 | Hashimoto |
| 2009/0005809 A1 | 1/2009 | Hess |
| 2011/0022099 A1 | 1/2011 | Ashman |
| 2013/0231667 A1 | 9/2013 | Taylor |
| 2013/0345752 A1 | 12/2013 | Hendren |
| 2014/0276830 A1 | 9/2014 | Cheney |
| 2014/0277516 A1 | 9/2014 | Miller |
| 2014/0358187 A1 * | 12/2014 | Taber ..................... A61B 17/10 606/86 R |
| 2015/0133940 A1 | 5/2015 | Palmer |
| 2015/0313592 A1 | 11/2015 | Coillard-Lavirotte |
| 2017/0000482 A1 * | 1/2017 | Averous ............ A61B 17/0642 |
| 2017/0252036 A1 | 9/2017 | Palmer et al. |
| 2018/0271521 A1 * | 9/2018 | Wahl ................. A61B 17/0682 |
| 2018/0344316 A1 | 12/2018 | Palmer |
| 2019/0046182 A1 | 2/2019 | Krumme |
| 2019/0069892 A1 * | 3/2019 | Biedermann ........ A61B 17/064 |
| 2019/0105040 A1 | 4/2019 | Gordon |
| 2020/0000046 A1 | 1/2020 | Orschulik |
| 2020/0038076 A1 | 2/2020 | Amis |
| 2020/0046345 A1 | 2/2020 | Zink |
| 2021/0298748 A1 | 9/2021 | Campbell |
| 2021/0330324 A1 | 10/2021 | Biedermann |
| 2021/0386422 A1 | 12/2021 | Maclure |
| 2022/0211368 A1 | 7/2022 | Hartdegen |
| 2023/0000488 A1 | 1/2023 | Palmer |
| 2023/0172647 A1 | 6/2023 | Knight |
| 2023/0200809 A1 | 6/2023 | Wahl |

FOREIGN PATENT DOCUMENTS

| | | |
|---|---|---|
| FR | 2694696 | 2/1994 |
| FR | 3023468 | 1/2016 |
| GB | 793126 | 4/1958 |

(56) References Cited

FOREIGN PATENT DOCUMENTS

| IL | 64726 | 2/1985 |
|---|---|---|
| WO | 9616603 | 6/1996 |
| WO | 2006077878 | 7/2006 |
| WO | 201288575 | 7/2012 |

OTHER PUBLICATIONS

Memometal Inc. USA, Easy Clip SI brochure, Aug. 12, 2009.
U. Rethnam et al., "Mechanical Characteristics of Three Staples Commonly Used in Foot Surgery," Journal of Foot and Ankle Research (Feb. 25, 2009).

* cited by examiner

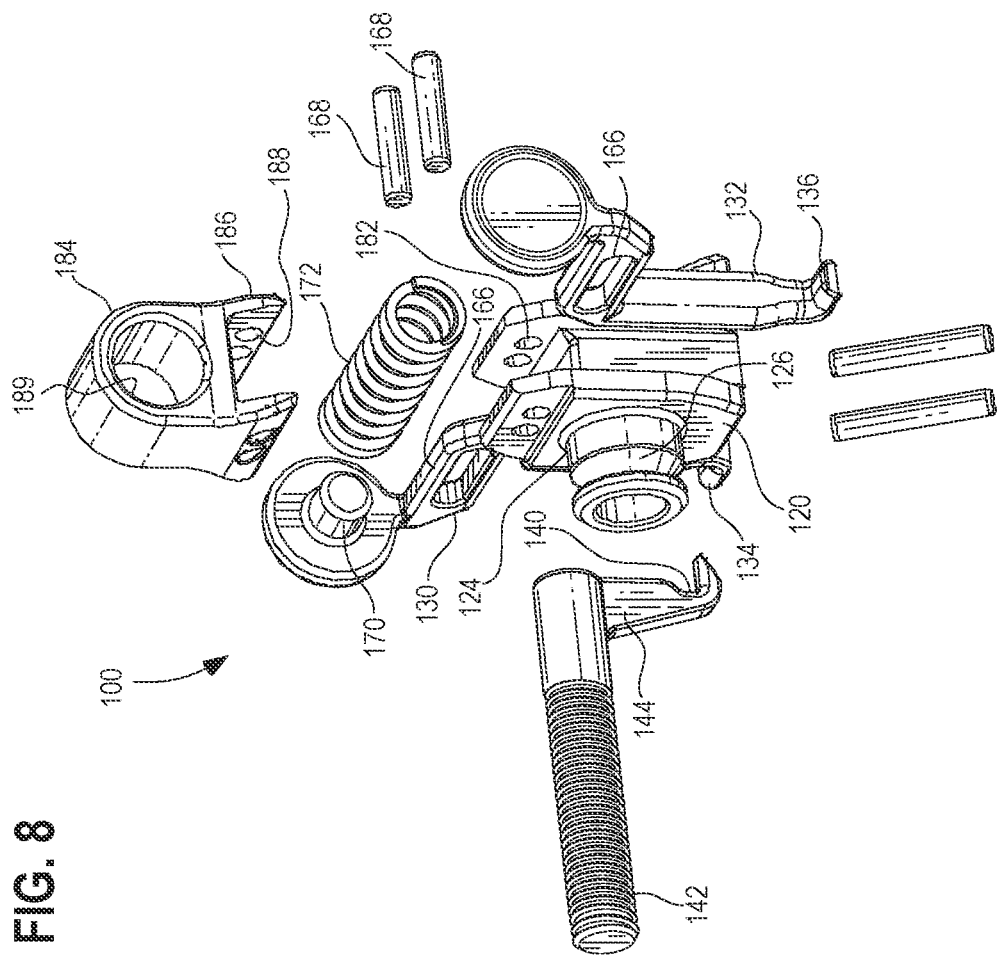
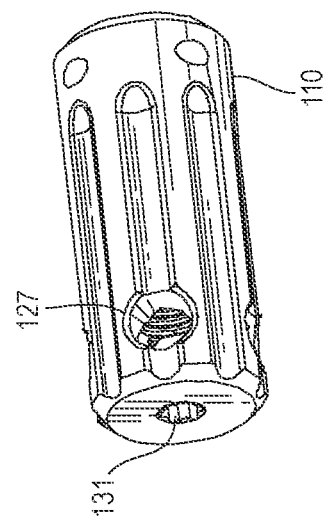
FIG. 8

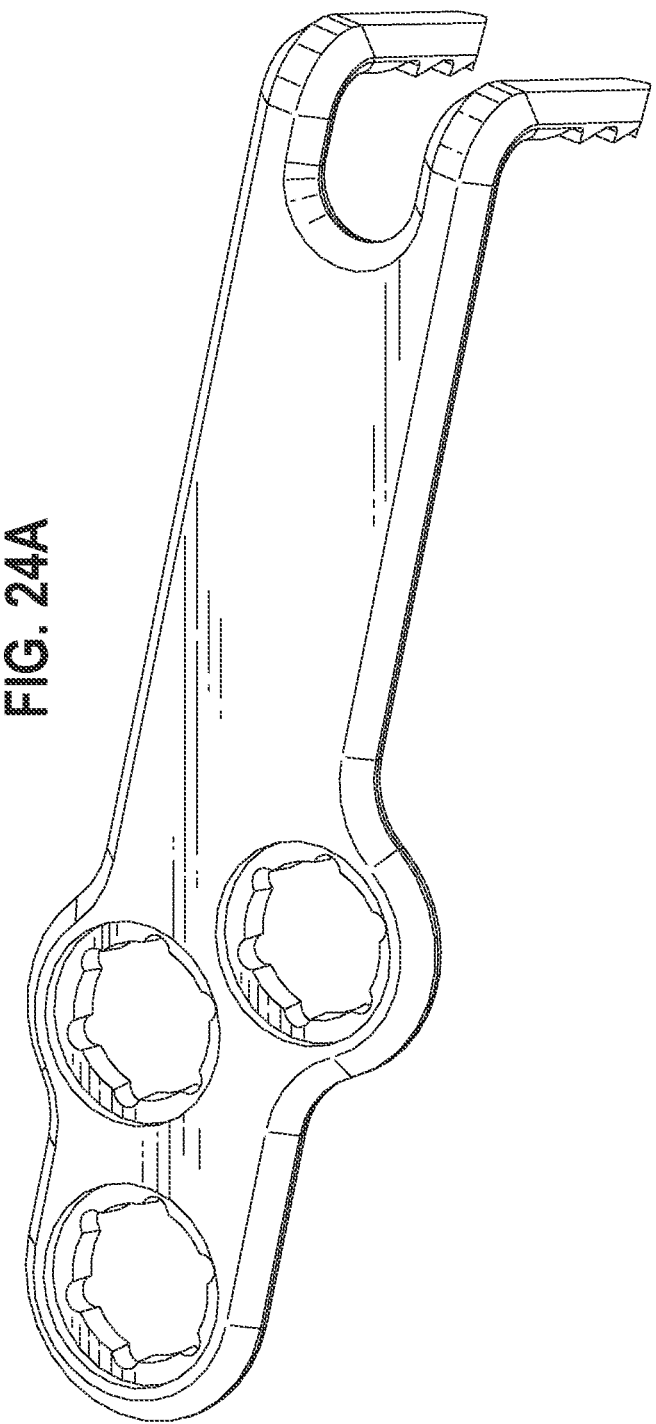
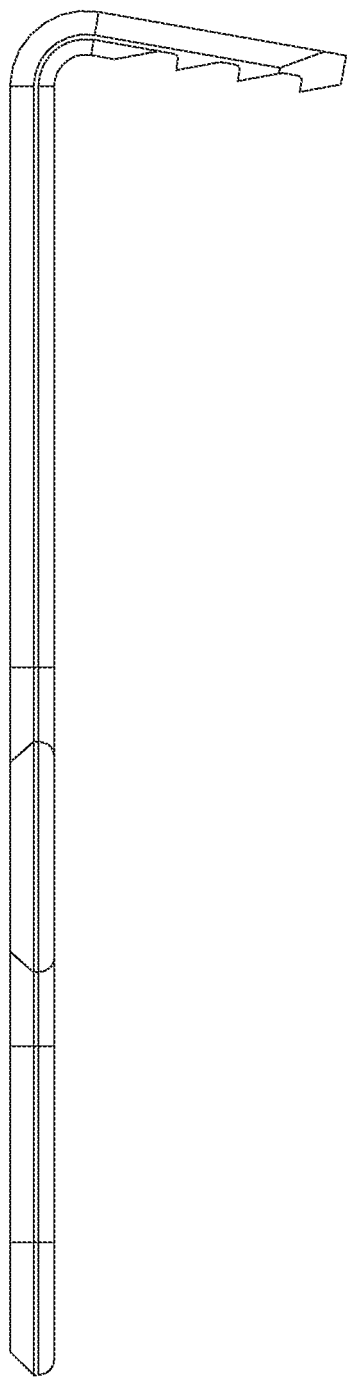
FIG. 24A
FIG. 24B

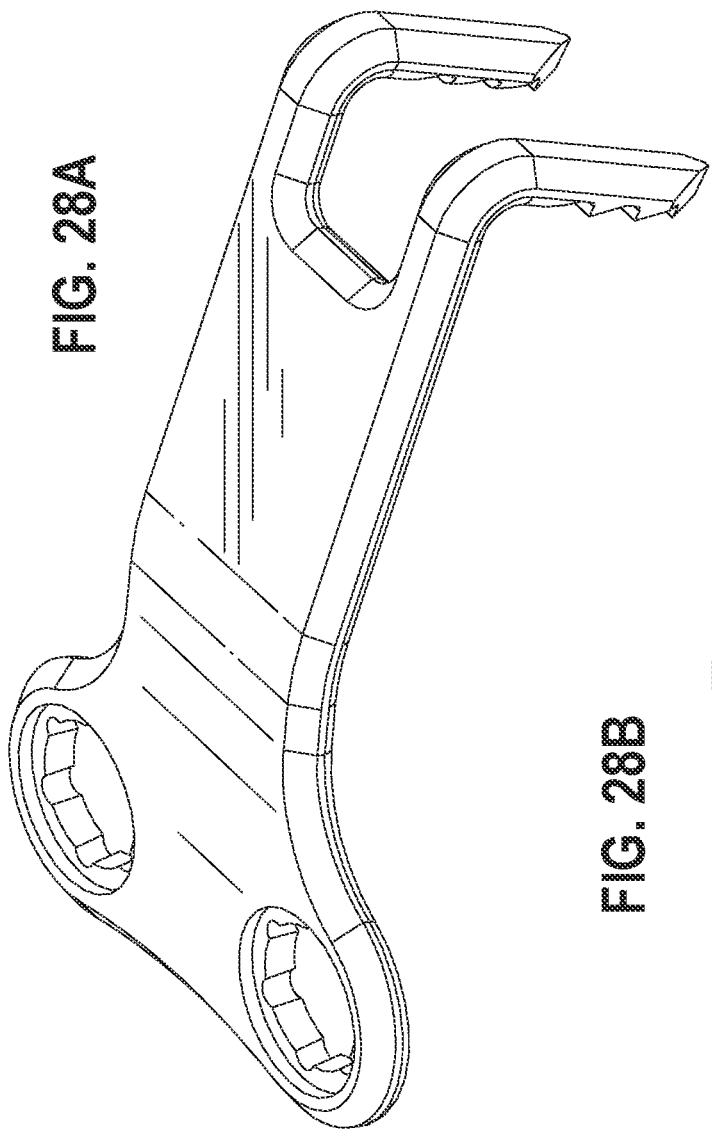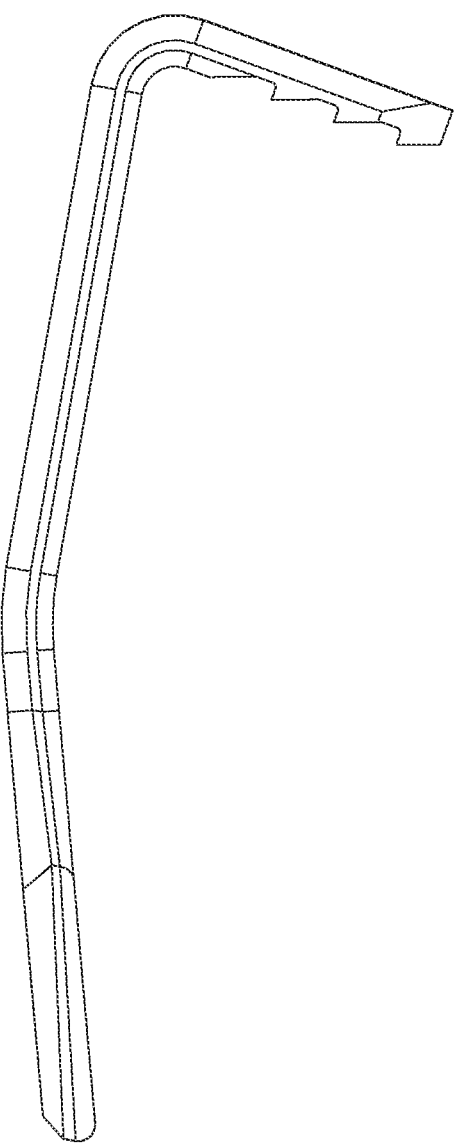

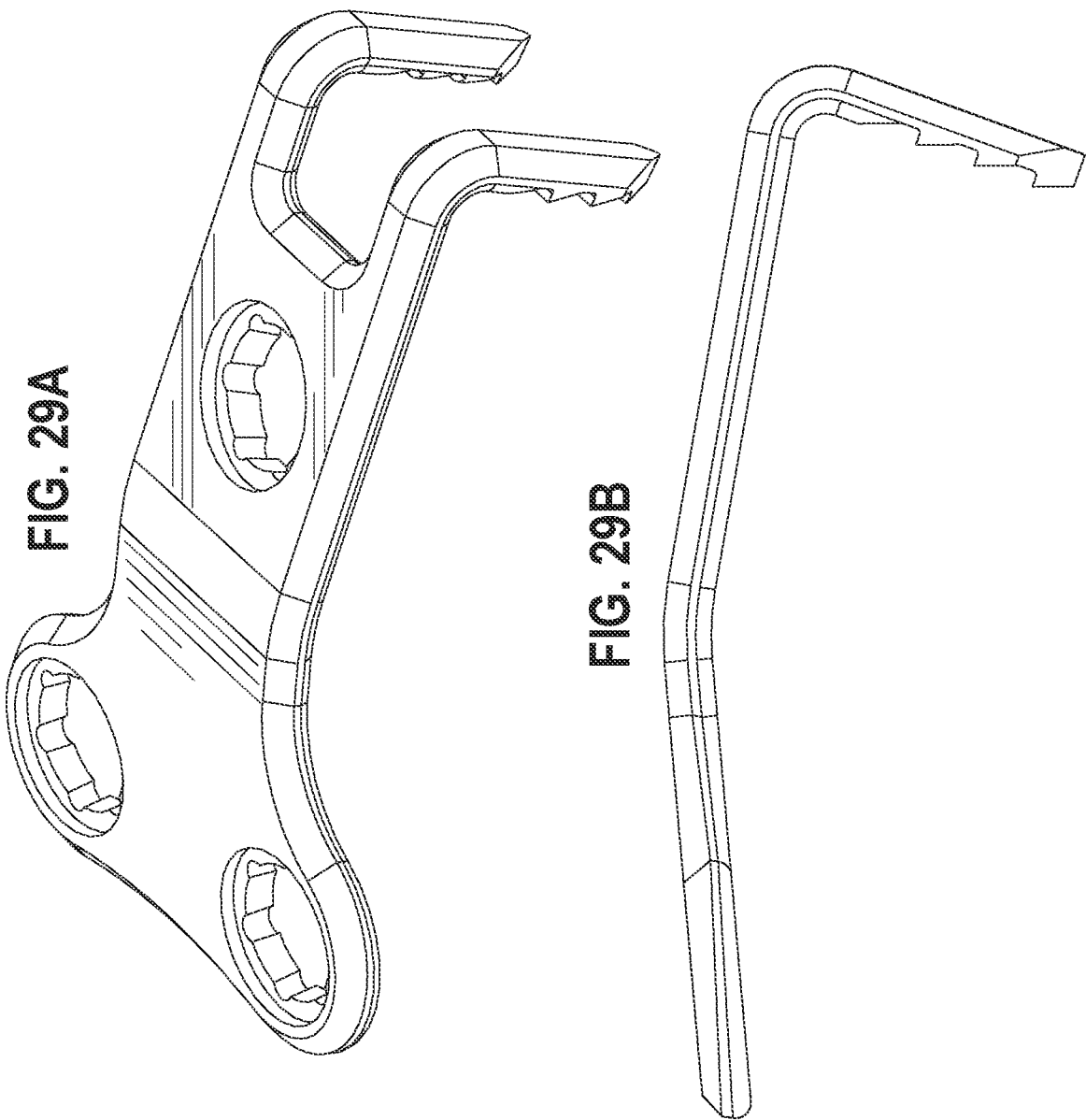

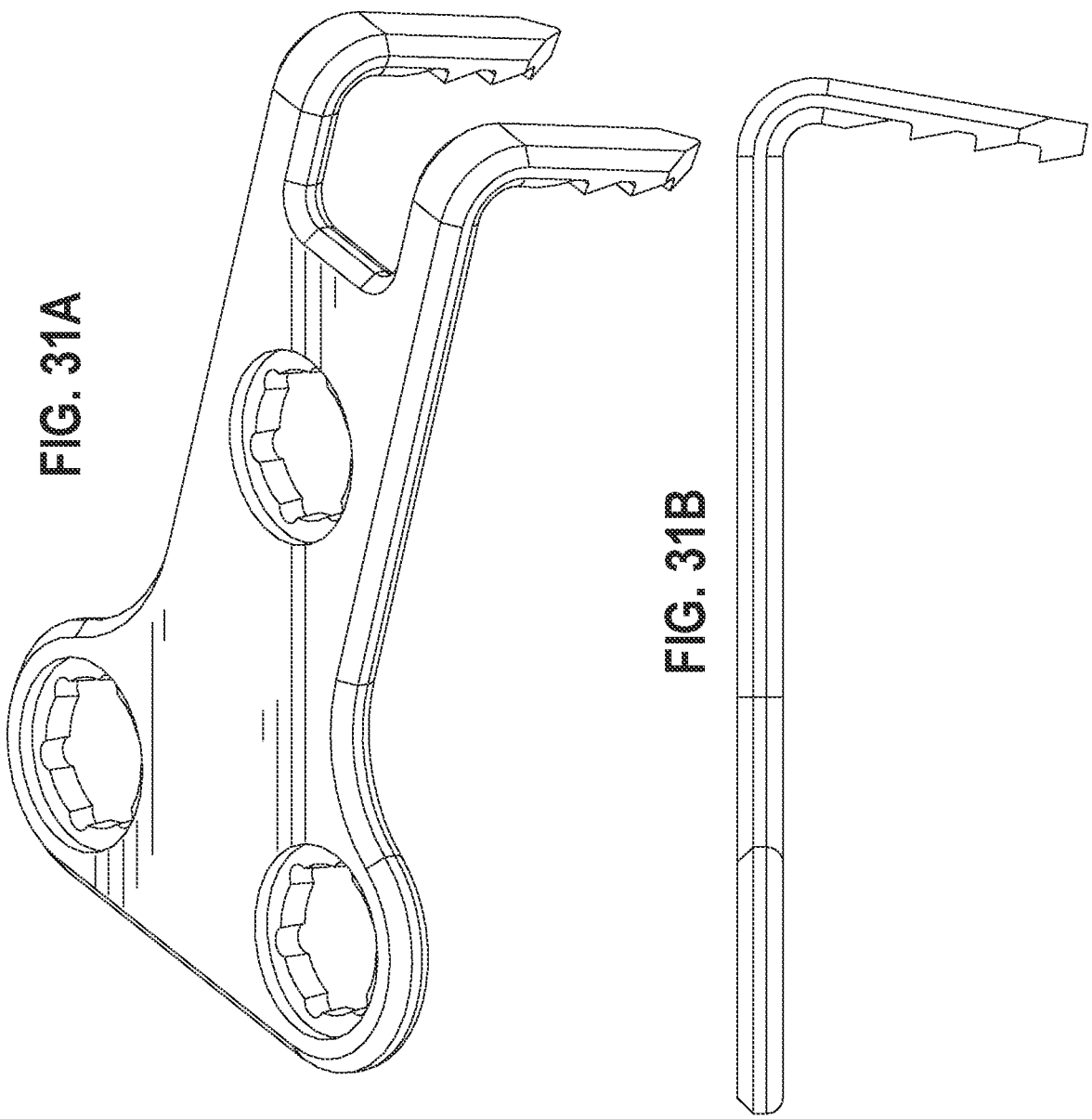

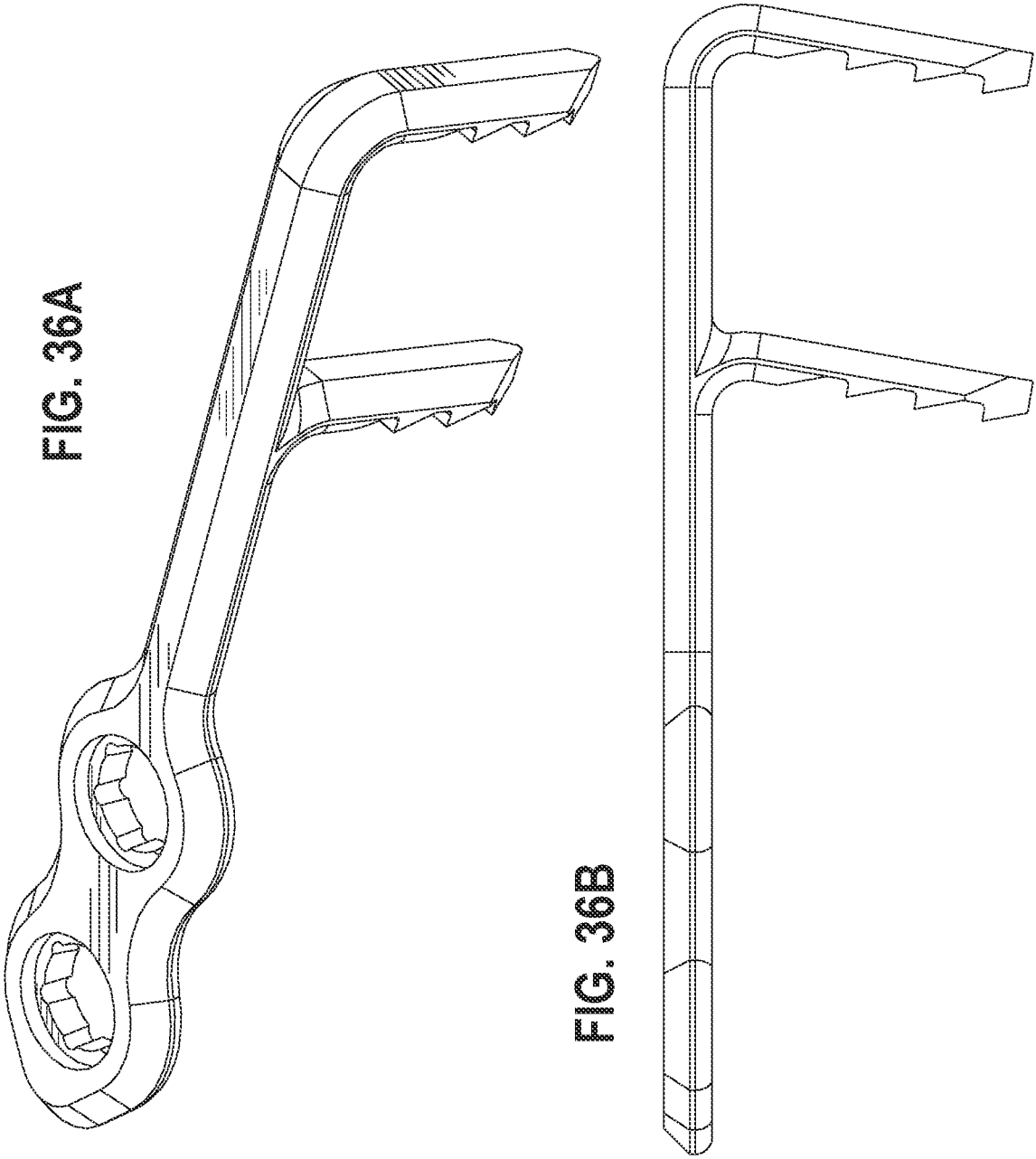

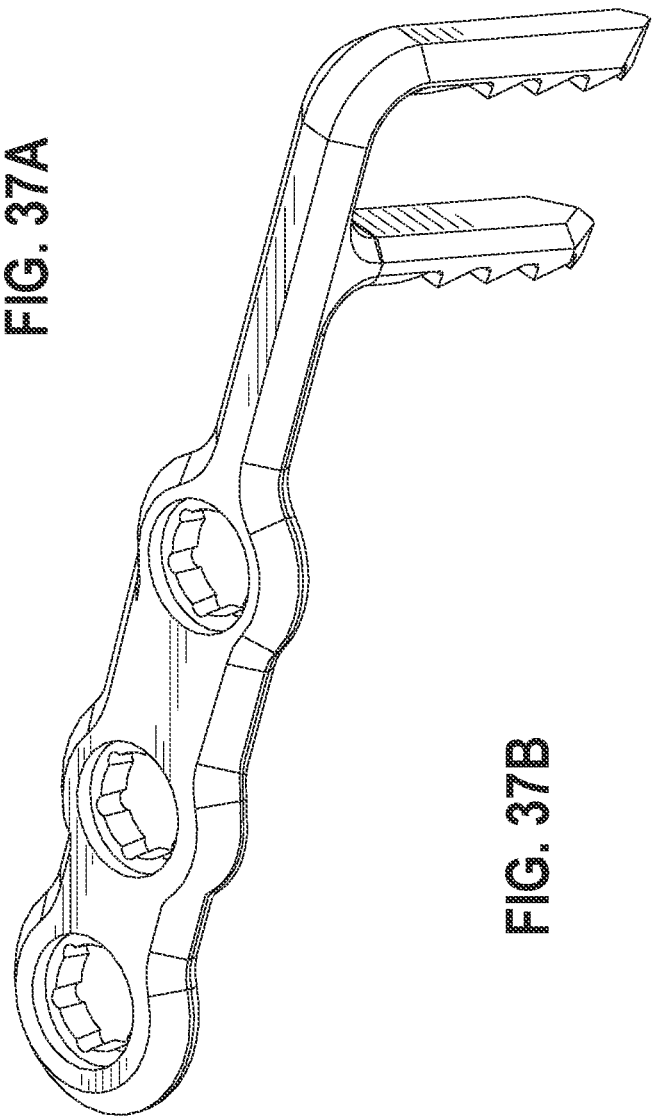
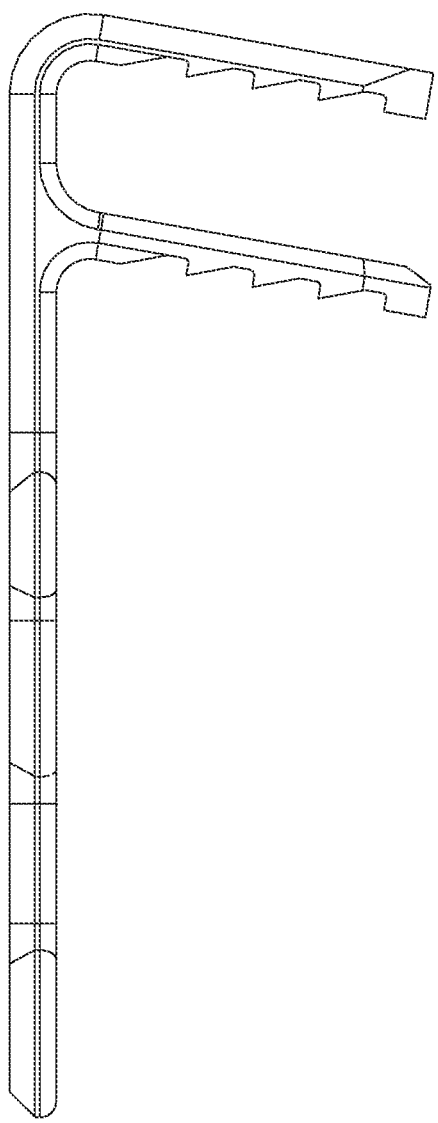
FIG. 37A
FIG. 37B

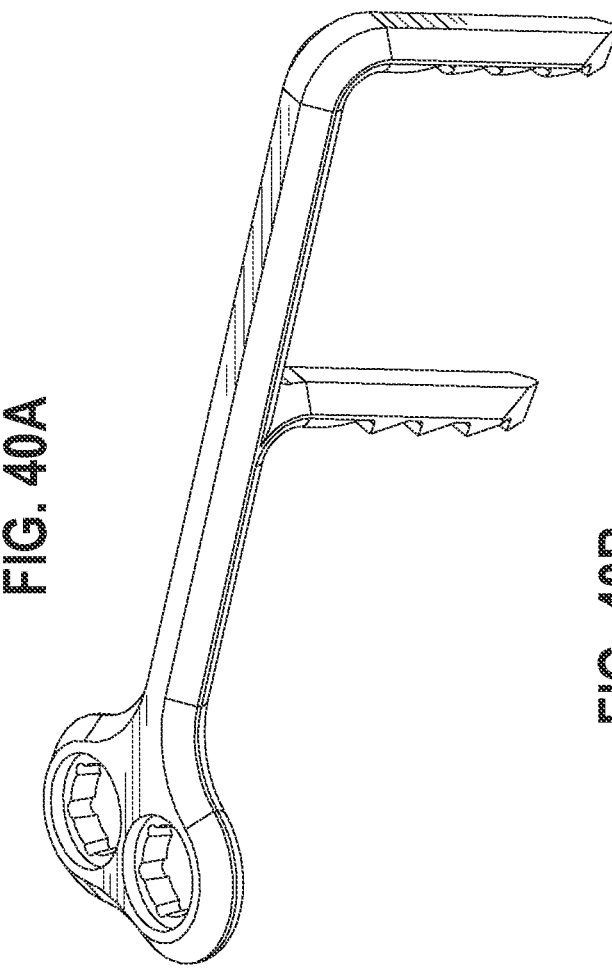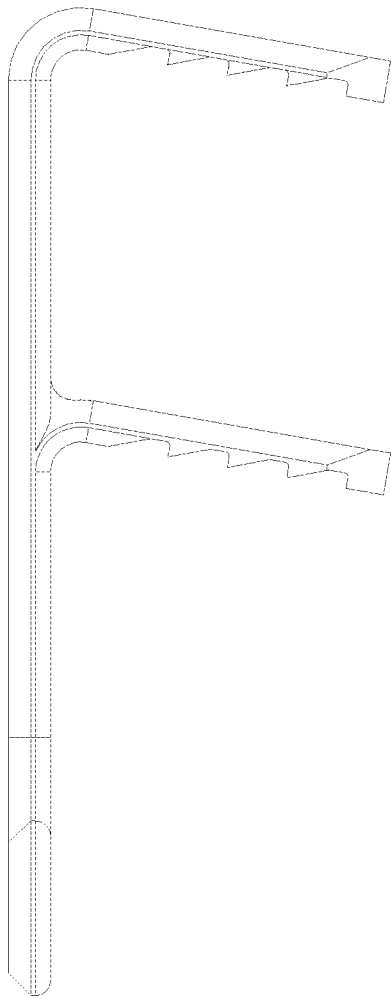
FIG. 40A
FIG. 40B

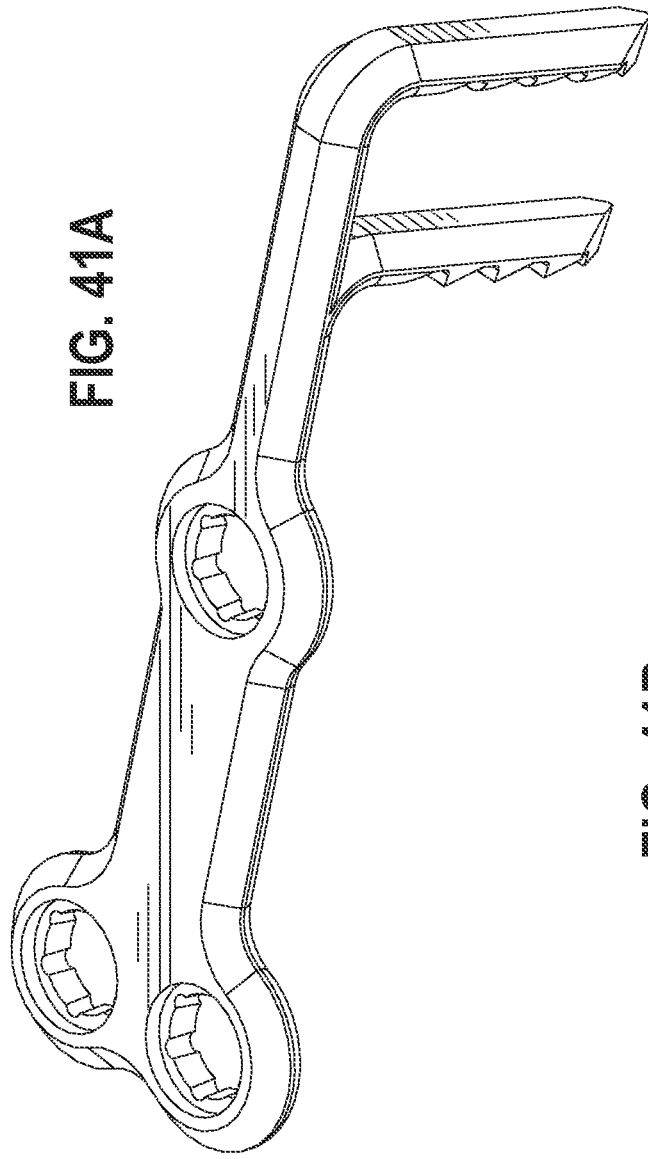
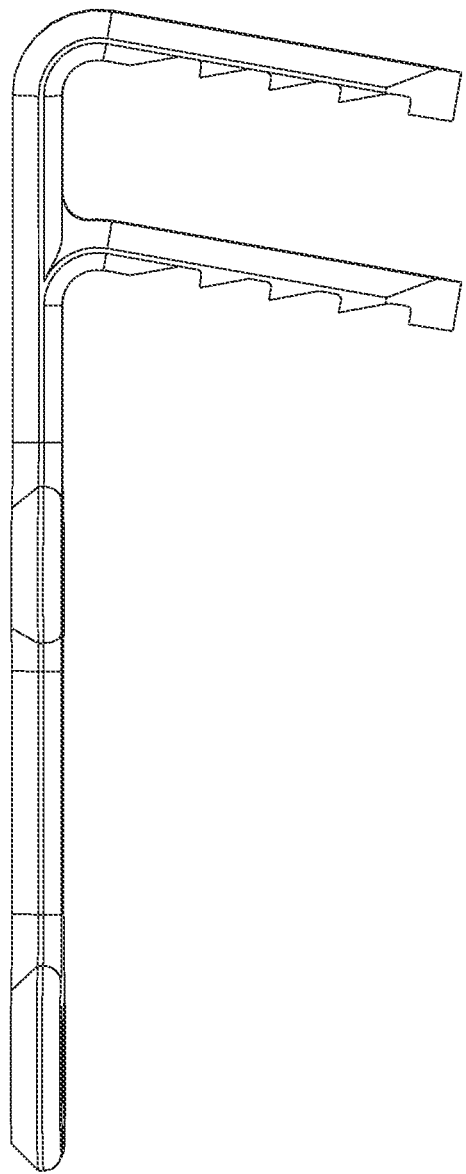
FIG. 41A
FIG. 41B

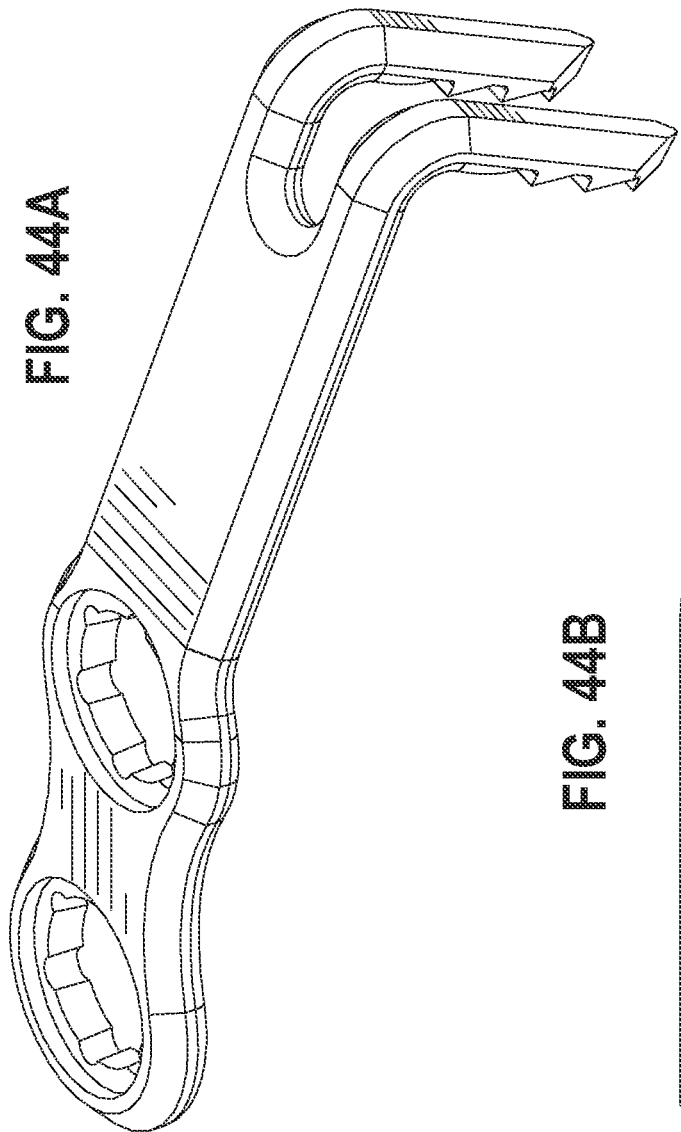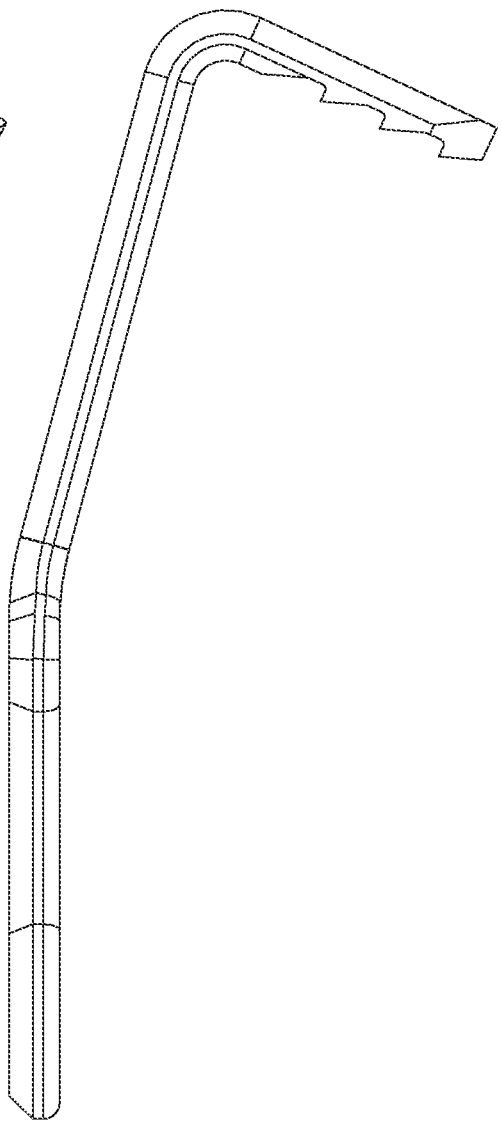

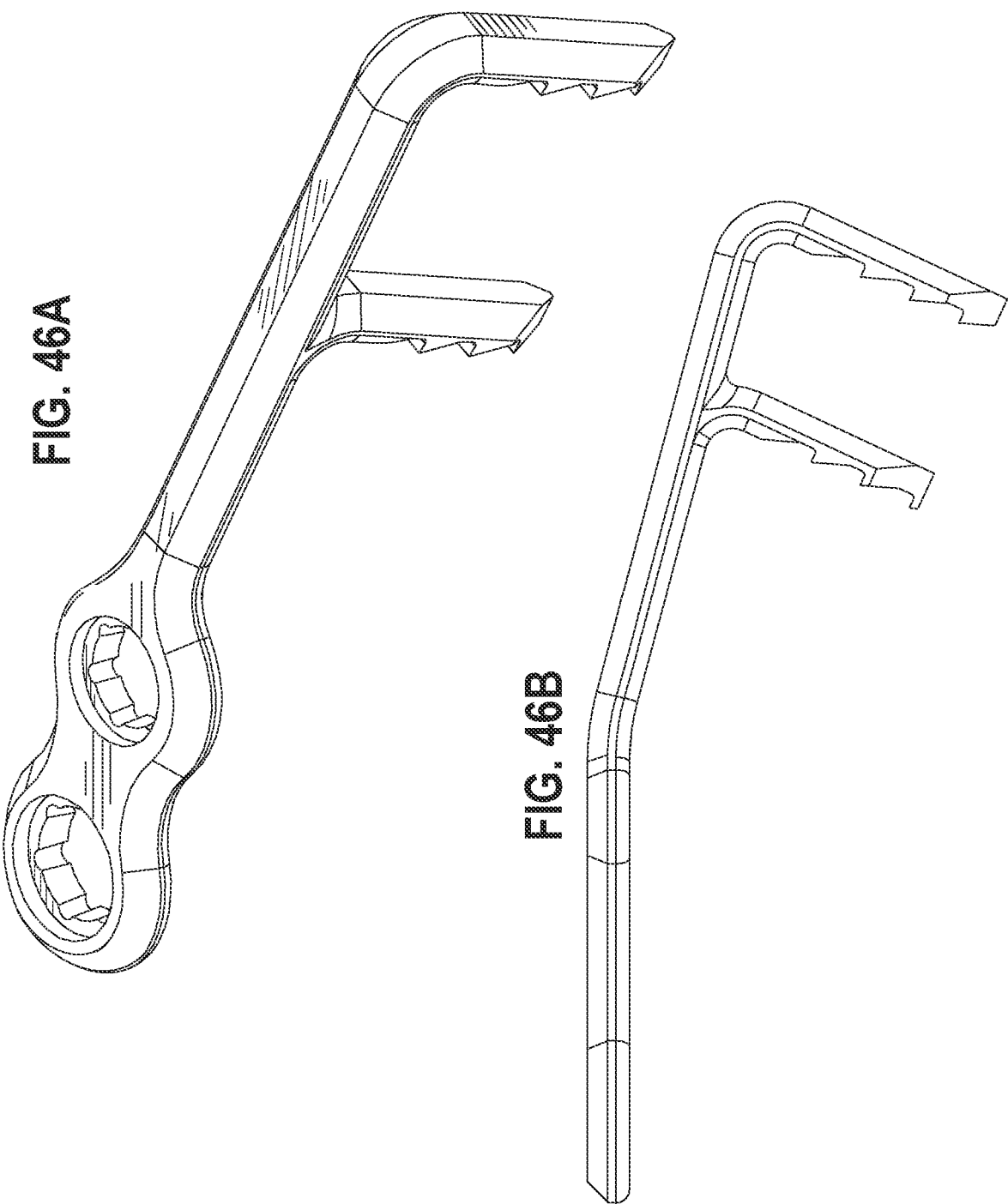

APPARATUS AND METHODS FOR JOINING BONES

FIELD

Apparatus and methods for joining or fusing two bones together are described herein and, more specifically, apparatus and methods for attaching to the bones a plate having legs at one end portion and at least one opening for bone screws at an opposite end portion.

BACKGROUND

Screws are commonly used for joining or fusing two bones or bone pieces together. The screw or screws may cross a joint, fracture or osteotomy. For example, screws can be used to fuse metatarsal phalangeal (MTP) joints to relieve pain or correct deformity. By way of another example, screws can be used in a Lapidus procedure to fuse the joint between the first metatarsal bone and the medial cuneiform.

Instead of screws, fusions can be made using one or more plates. In one form, plates have legs at one end and screw holes at another end. A spreader tool can abut the legs to bend the legs from an acute angle to a large angle by pushing against an opening in the body of the plate. Disadvantageously, such a spreader tool can require specialized openings in the body for receiving part of the tool. Moreover, unnecessary openings in the body—beyond those necessary for receiving the screws—can weaken the body. Furthermore, the requirement that the spreader tool contacts the opposite ends of the plate can limit the designs of plates that can be used with such a tool.

The plate insertion tools and methods described herein can address these problems.

BRIEF DESCRIPTION OF THE DRAWINGS

FIG. 8 is an exploded perspective view of the plate insertion tool of FIG. 1;

FIG. 24A is a perspective view and FIG. 24B is a side elevation view of a second embodiment of a plate having a body portion with a pair of legs at one thereof and three offset screw holes at an opposite end portion, the pair of legs being at an acute angle relative to the body;

FIG. 28A is a perspective view and FIG. 28B is a side elevation view of a sixth embodiment of a plate having a body portion with a pair of legs at one thereof and two transverse screw holes in an inclined, flared end portion of the body, the pair of legs being at an acute angle relative to the body;

FIG. 29A is a perspective view and FIG. 29B is a side elevation view of a seventh embodiment of a plate having a body portion with a pair of legs at one thereof and two transverse screw holes in an inclined, flared end portion of the body, the pair of legs being at an acute angle relative to the body, and an intermediate third screw hole in the body between the legs and the inclined, flared end portion of the body;

FIG. 31A is a perspective view and FIG. 31B is a side elevation view of a ninth embodiment of a plate having a body portion with a pair of legs at one thereof and two transverse screw holes in a flared end portion of the body, the pair of legs being at an acute angle relative to the body, and an intermediate third screw hole in the body between the legs and the flared end portion of the body;

FIG. 36A is a perspective view and FIG. 36B is a side elevation view of a fourteenth embodiment of a plate having a pair of legs depending from a linear extension and arranged in-line and two in-line screw holes in a body at an opposite end of the extension from the legs, the pair of legs each being at an acute angle relative to the extension;

FIG. 37A is a perspective view and FIG. 37B is a side elevation view of a fifteenth embodiment of a plate having a pair of legs depending from a linear extension and arranged in-line and two in-line screw holes in a body at an opposite end of the extension from the legs, the pair of legs each being at an acute angle relative to the extension, and an intermediate third screw hole in the body between the extension and the other three screw holes;

FIG. 40A is a perspective view and FIG. 40B is a side elevation view of an eighteenth embodiment of a plate having a pair of legs depending from a linear extension and arranged in-line and two transverse screw holes in a body at an opposite end of the extension from the legs, the pair of legs each being at an acute angle relative to the extension;

FIG. 41A is a perspective view and FIG. 41B is a side elevation view of a nineteenth embodiment of a plate having a pair of legs depending from a linear extension and arranged in-line and two transverse screw holes in a body at an opposite end of the extension from the legs, the pair of legs each being at an acute angle relative to the extension, and an intermediate third screw hole in the body between the extension and the other two screw holes;

FIG. 44A is a perspective view and FIG. 44B is a side elevation view of a twenty-second embodiment of a plate having a body portion with a pair of legs at one thereof and two in-line screw holes in an inclined end portion of the body, the pair of legs being at an acute angle relative to the body;

FIG. 46A is a perspective view and FIG. 46B is a side elevation view of a twenty-fourth embodiment of a plate having a pair of legs depending from a linear extension and arranged in-line and two in-line screw holes in an inclined end portion of the body at an opposite end of the extension from the legs, the pair of legs each being at an acute angle relative to the extension.

DETAILED DESCRIPTION

Figure 1:
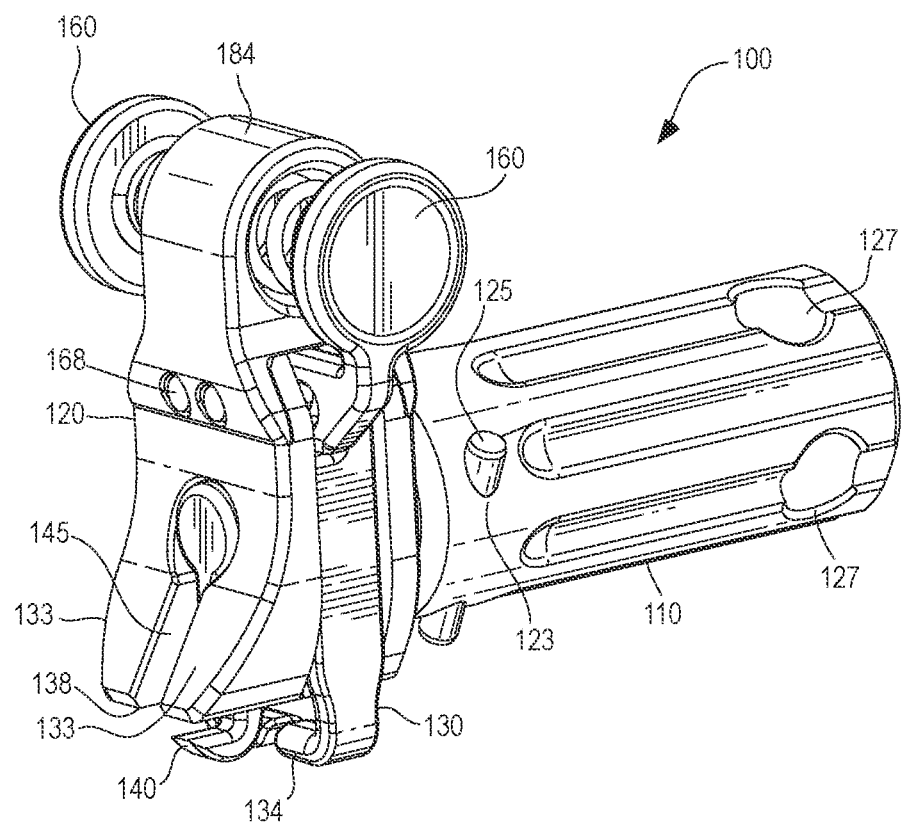
FIG. 1 is a perspective view of a plate insertion tool having a handle rotatably mounted to a head, a pair of arms slidable relative to the head, and a pusher finger.

A plate insertion tool is provided for use with a plate, such as a compression plate, having a body portion with one or more apertures each for receiving a screw and a pair of legs at one end that are each connected to the body at an acute angle and spaced apart by a shoulder, the plate insertion tool being usable to temporarily tension the legs prior to insertion into holes in a bone. The plate insertion tool includes a pair of facing, inwardly extending fingers being movable between a clamping position for clamping therebetween, in use, the legs of the plate, and an open position where, in use, the inwardly extending fingers are spaced from the legs of the plate. The pair of inwardly extending fingers are closer to each other in the clamping position as compared to the open position. The plate insertion tool also includes a pushing finger movable between a retracted position and an extended position relative to the pair of inwardly extending fingers and positioned for engaging, in use, the shoulder of the plate such that when the pushing finger moves to the extended position the legs are temporality tensioned by bending the legs away from the body.

A system for joining bones together is also provided, where the system includes a plate having a body portion with one or more apertures each for receiving a bone screw and a pair of legs at one end that are each connected to the body at an acute angle and spaced apart by a shoulder. The system also includes the plate insertion tool.

A method of using the system is also provided, where the method includes drilling a pair of guide holes for receiving the legs of the compression plate; clamping the compression plate relative to the plate insertion tool by moving the pair of inwardly extending fingers from the open position to the clamping position; engaging the shoulder of the compression plate with the pusher finger; moving the pusher finger toward the extended position to temporality tension the legs by pivoting the legs away from the body of the compression plate to a greater angle relative to the body as compared to the acute angle; and inserting the legs of the compression plate into the guide holes when the legs are pivoted away from the body to the greater angle.

As described herein and illustrated in FIGS. 1-23 apparatus and methods are provided for using a plate to fuse bones together. Generally, the plate has a body portion with one or more apertures or screw holes each for receiving a screw and a pair of legs side-by-side at one end that are each connected to the body at an acute angle and spaced apart by a shoulder. The legs are inserted into pre-drilled guide holes in one of the bones and one or more screws are inserted through the apertures and into another of the bones to secure the plate to the bones. A plate insertion tool can be used to temporarily tension the legs prior to insertion into holes in a bone by bending or pivoting the legs away from the body, as will be described further herein. Advantageously, the plate insertion tool only needs to contact one end portion of the plate to tension the legs. Also advantageously, specific holes in the plate are not needed for the plate insertion tool to tension the legs.

Figure 2:
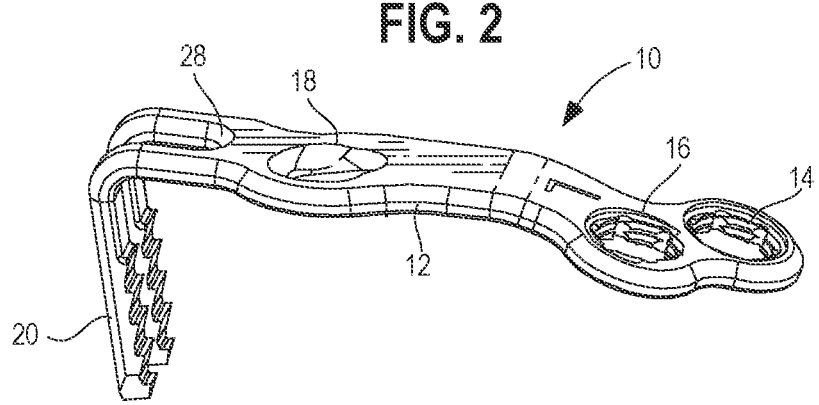
FIG. 2 is a side perspective view of an exemplary embodiment of a plate having a body portion with three apertures each for receiving a screw and a pair of legs at one end that are each connected to the body at an acute angle and spaced apart by a shoulder.
Figure 3:
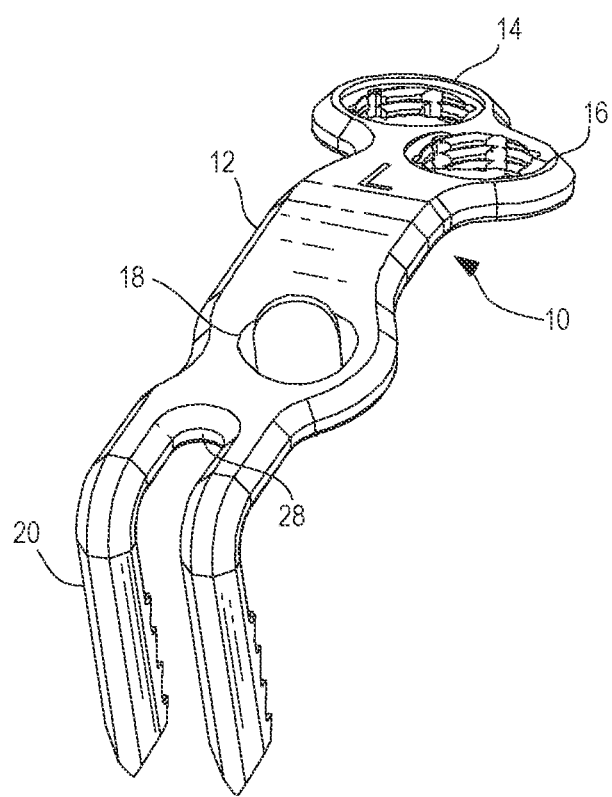
FIG. 3 is a front perspective view of the plate of FIG. 2.
Figure 15:
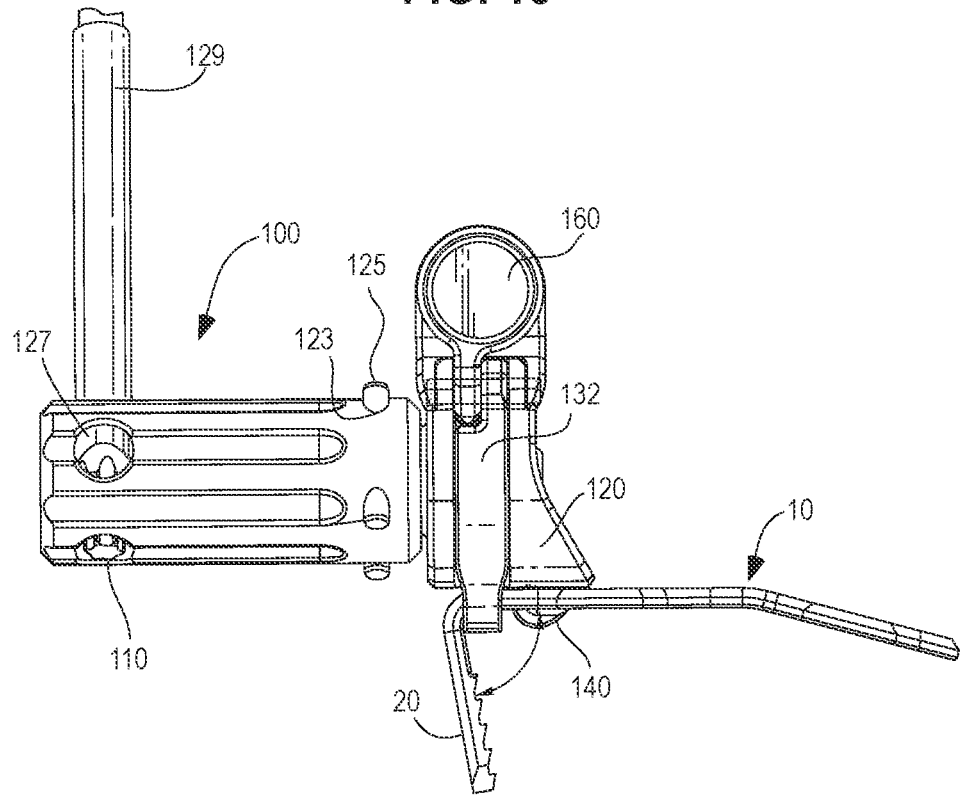
FIG. 15 is a side elevation view of the arrangement of the plate insertion tool and plate of FIG. 14, showing the pusher finger in the retracted position.
Figure 16:
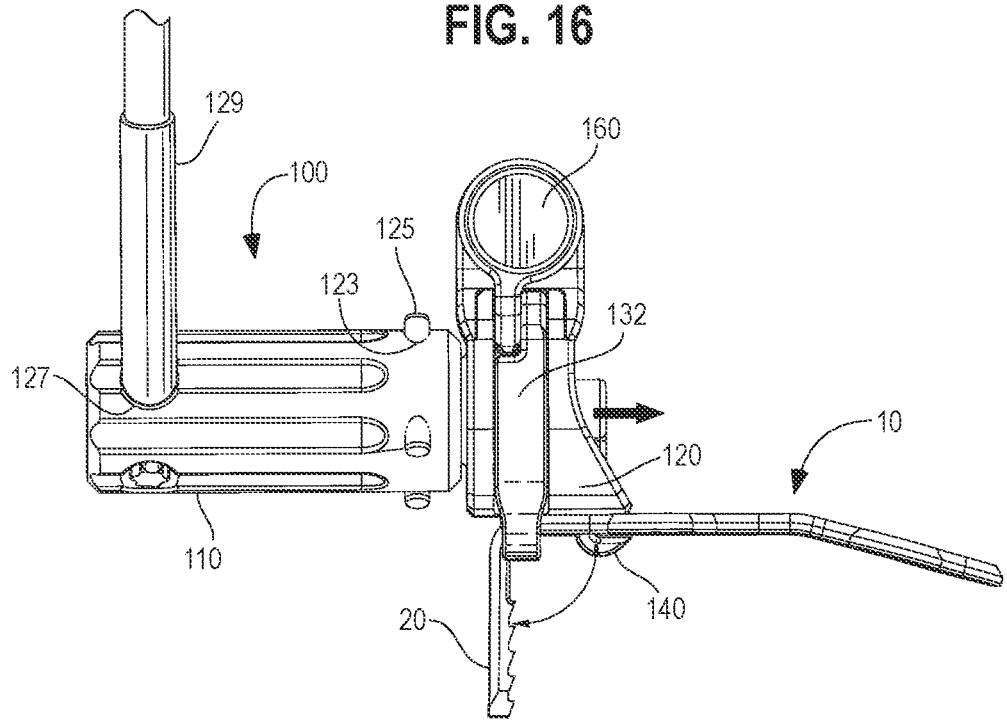
FIG. 16 is a side elevation view of the arrangement of the plate insertion tool and plate similar to that of FIG. 15, but showing the handle having been rotated to move the pusher finger to the extended position abutting the shoulder to pivot the pair of legs to an increased angle, generally perpendicular, as compared to the acute angle shown in FIG. 15.

Turning to details of a first exemplary embodiment of the plate 10, shown in FIGS. 2 and 3, the plate 10 has a body portion 12 with three apertures 14, 16, 18 each for receiving a screw 22, 24, 26 and a pair of legs 20 that are parallel and arranged side-by-side at one end thereof with a shoulder 28 therebetween. The legs 20 are each connected to the body 12 of the plate 10 at an acute angle, as shown in FIGS. 2 and 15. The plate 10 can be a compression plate, e.g., made of a shape-memory material, such as nitinol. Thus, when the legs 20 are pivoted away from the body 12 to a perpendicular or toward a perpendicular arrangement relative to the body 12 (e.g., increasing the angle of the legs relative to the body), such as shown in FIG. 16, they have a bias to return to their original orientation. This bias can be used advantageously during and after insertion of the legs 20 into pre-drilled guide holes 32 in a bone 30 to tension the plate 10 and thereby compress adjacent bones 30, 40 together, particularly when the pre-drilled guide holes 32 are generally perpendicular or at least at a greater angle than the acute angle of the original orientation. The plate insertion tool 100 is used to not only to pivot the legs 20 of the plate 10 rearwardly, but also to maintain that pivoted arrangement of the legs during insertion into the pre-drilled guide holes.

The plate 10 shown in FIGS. 2 and 3, includes two screw holes in the body thereof at an end portion of the body opposite the legs. Those two screw holes are preferably, though not necessarily, configured with internal threads for engaging with external threads on the heads of the screws. The plate 10 also includes an intermediate or third screw hole in the body that is intermediate the legs and the other two screw holes. This intermediate screw hole, if present, can optionally be used for a bridging screw that passes through one bone and at least partially into another.

The plate insertion tool includes a handle 110 that is rotatably mounted to a head 120, as shown generally in FIGS. 1 and 5-7. A pair of arms 130, 132 are slidably secured to the head 120, and can slide toward and away from each other. Ends of the arms 130, 132 each include an inwardly extending finger 134, 136. The inwardly extending fingers 134, 136 are arranged to face each other and are spaced from bottom surfaces 122 of the head. Movement of the arms 130, 132 toward and away from each other likewise moves the fingers 134, 136 toward each other, into a clamping position, and away from each other, into an open position. A pusher finger 140 is extensible relative to the handle 110 and the head 120 and is moveable from a retracted position, shown in FIG. 11, to an extended position, shown in FIG. 12.

Figure 13:
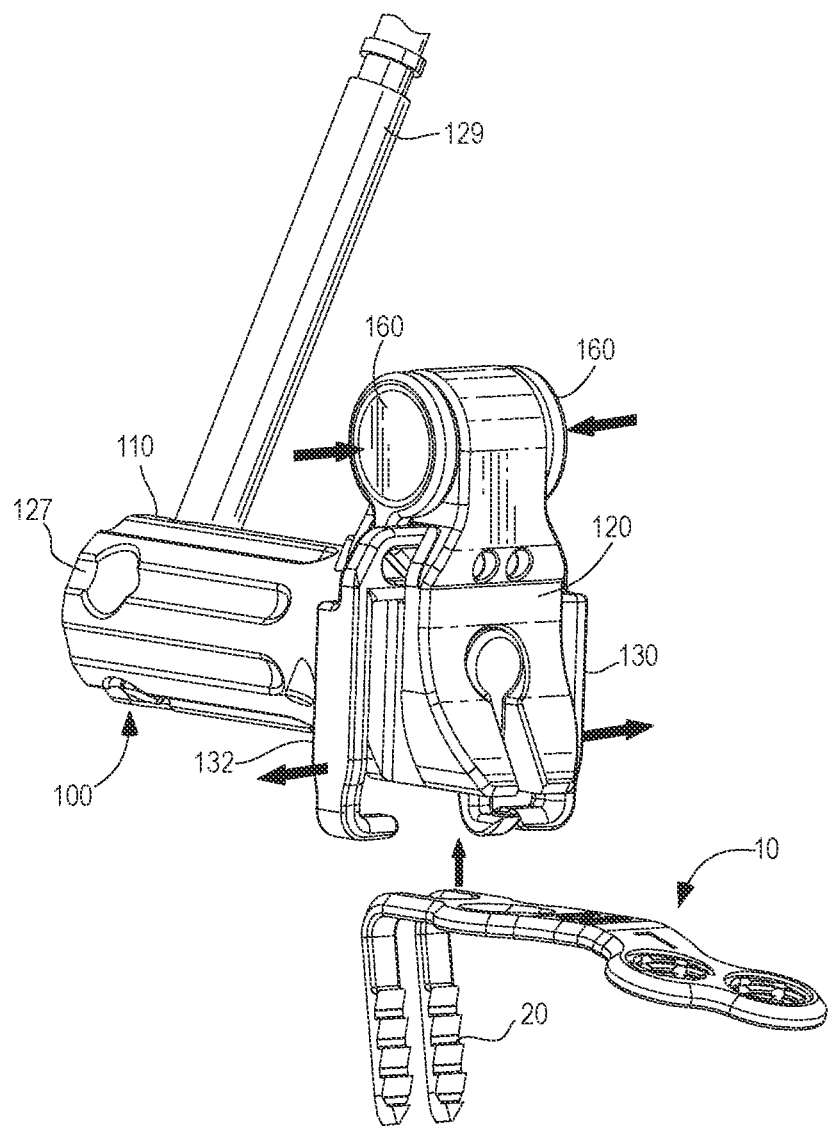
FIG. 13 is a perspective view of the plate insertion tool of FIG. 1 in combination with the plate of FIG. 2, showing the actuators of the arms being pushed toward each other to slide the inwardly extending fingers away from each other to their open position such that the plate can be moved against the bottom of the head of the tool.
Figure 14:
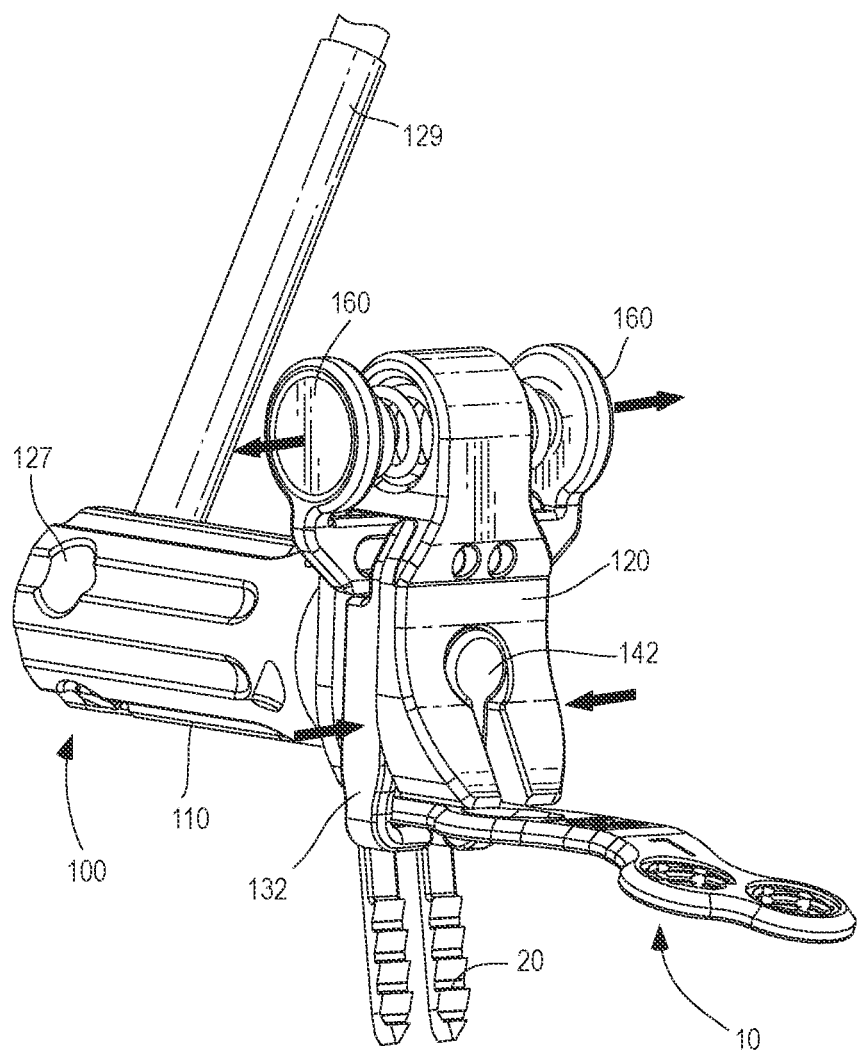
FIG. 14 is a perspective view of the plate insertion tool of FIG. 1 in combination with the plate of FIG. 2, showing the actuators of the arms being moved away each by the biasing force of the spring to slide the inwardly extending fingers toward each other to their clamping position such that the plate is clamped against the bottom of the head of the tool by the inwardly extending fingers.

When used with the plate 10 of FIGS. 2 and 3, the pair of inwardly extending fingers 134, 136 of the arms 130, 132 are movable between a clamping position for clamping therebetween the legs 20 of the plate 10, as shown in FIG. 14 and an open position where the inwardly extending fingers 134, 136 are spaced from the legs 20 of the plate 10, as shown in FIG. 13. When the plate insertion tool 100 is clamping the plate 10, as shown in FIG. 14, the pusher finger 140 can move from its retracted position, shown in FIG. 15, to the extended position, shown in FIG. 16, relative to the pair of inwardly extending fingers and engage with and push the shoulder of the plate away from the legs to temporarily tensioned the legs by bending the legs away from the body to an angle generally perpendicular relative to the adjacent portion of the body (or at least an increased angle relative to the body or, in other words, less acute of an angle).

Figure 17:
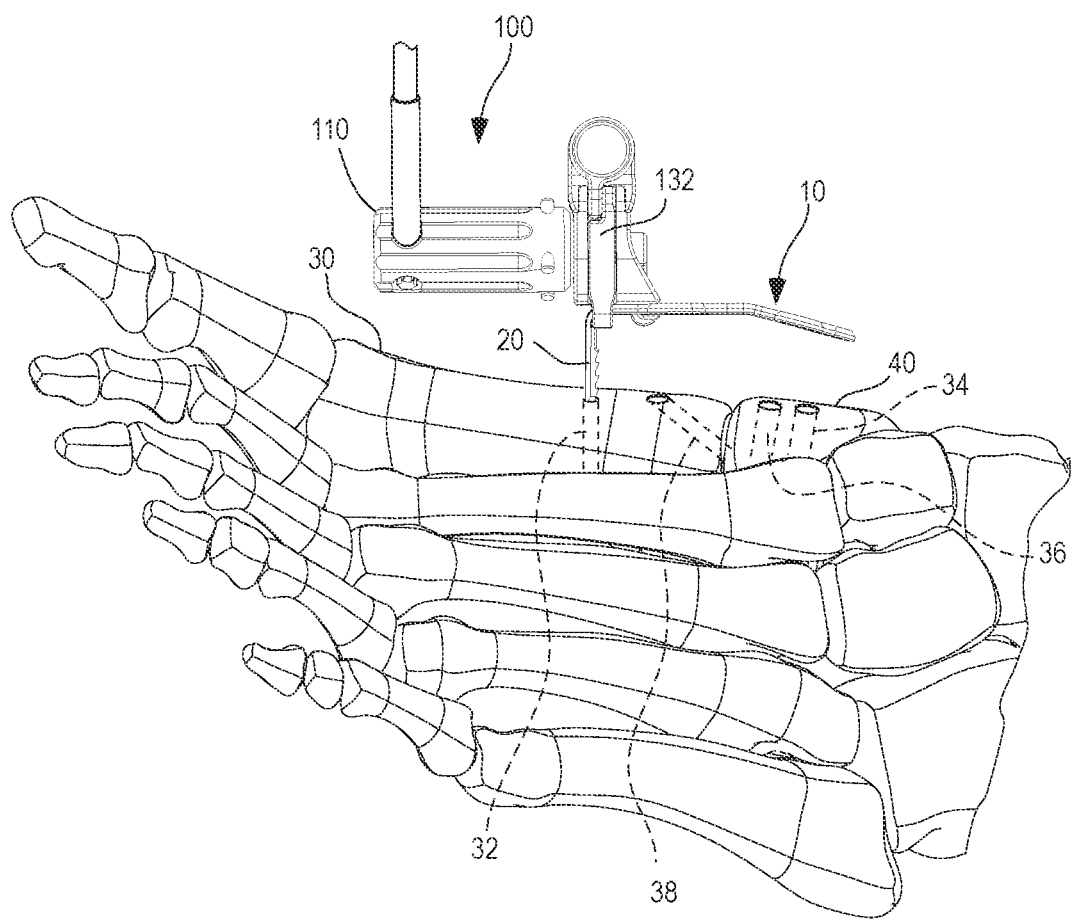
FIG. 17 is a side elevation view of the arrangement of the plate insertion tool and plate of FIG. 16, with the legs starting to be inserted into pre-drilled guide holes in the first metatarsal.
Figure 18:
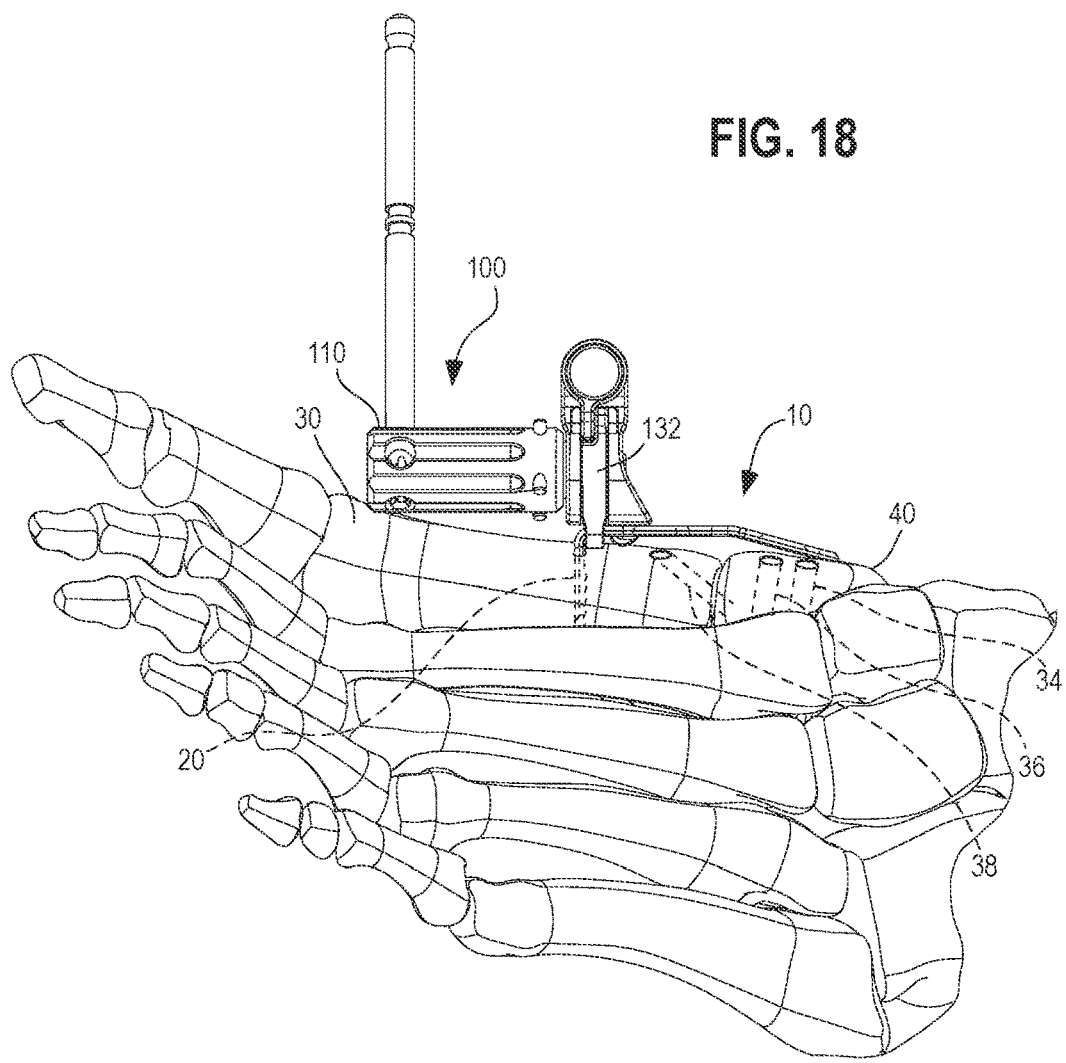
FIG. 18 is a side elevation view of the arrangement of the plate insertion tool and plate of FIG. 16, with the legs being further inserted into the pre-drilled guide holes in the first metatarsal as compared in FIG. 17.
Figure 19:
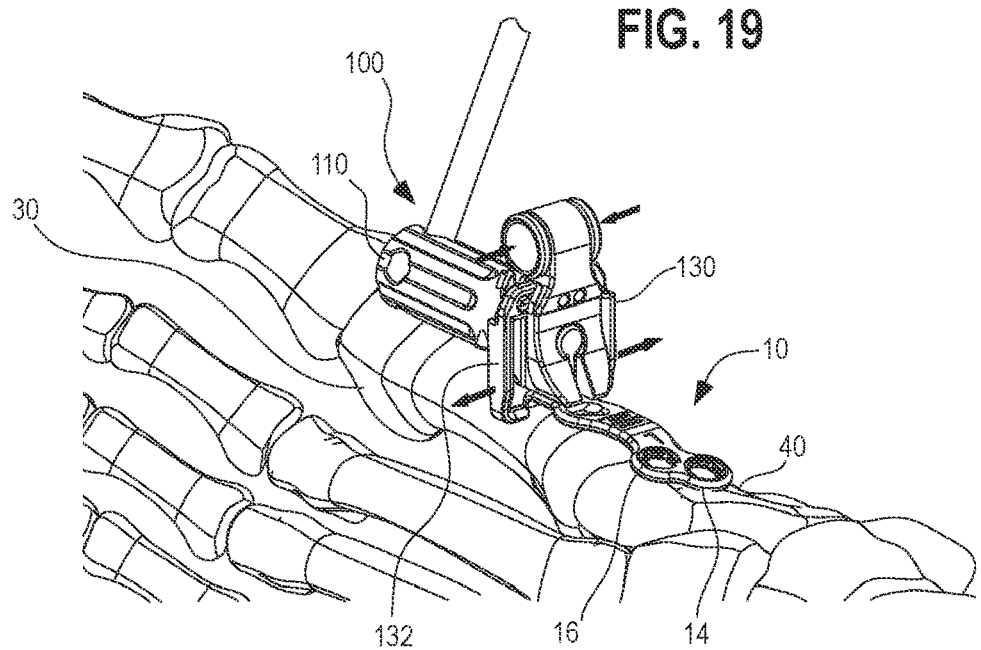
FIG. 19 is a perspective view of the arrangement of the plate insertion tool and plate shown in FIG. 18.

When the plate 10 is clamped and the legs are temporarily tensioned, as shown in FIG. 16, the legs of the plate can be inserted into a pair of predrilled guide holes in a bone, as shown in FIGS. 17 and 18. The predrilled guide holes can be formed, for example, using a template to ensure the spacing. When the legs are nearly all the way inserted into the guide holes (the underlying inwardly extending fingers of the arms prevent complete insertion), the plate insertion tool can be disconnected from the plate to allow the legs to be inserted further into the guide holes. The plate insertion tool is disconnected from the plate by firstly moving the pusher finger to its retracted position and then secondly moving the arms away from each other to move the inwardly extending fingers from their clamping position to their open position, as shown in FIG. 19.

After the legs of the plate have been inserted into the pre-drilled guide holes in one of the bones to be fused, the screws can then be inserted through the screw holes body of the plate and into the other of the bones to be fused. Optionally, the plate can be tensioned and then the screws inserted. By having the plate attached to the other of the bones under tension, compression or additional compression between the two adjacent bones can result, thereby improving the fusion of the two bones, which can take advantage of Wolff's Law. As used herein, the term fused can include reducing or stabilizing a fracture or osteotomy. Also as used herein, when bones or a pair of bones or adjacent bones are mentioned, that can include what was a single bone but is fractured or otherwise separated.

Figure 20:
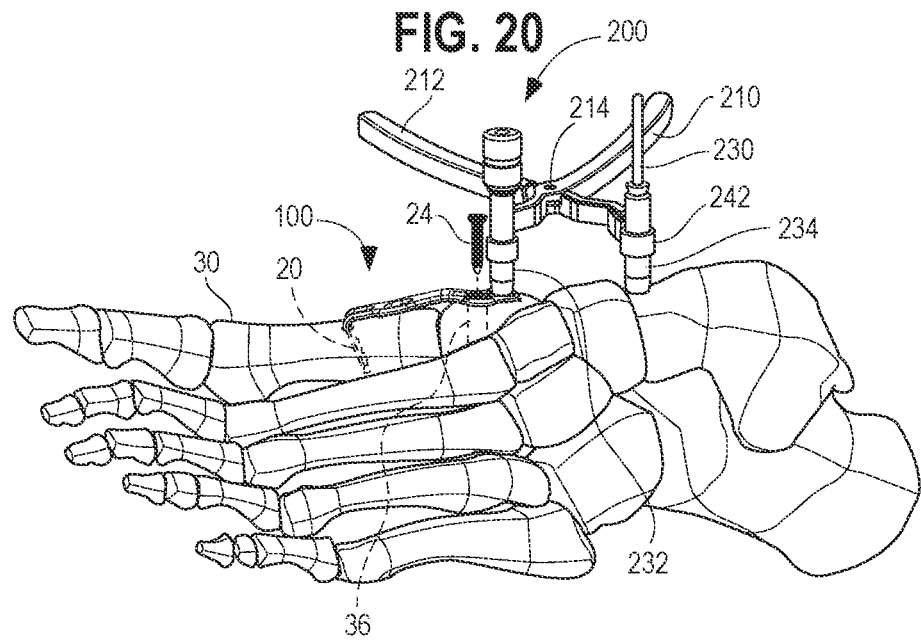
FIG. 20 is a perspective view of a tensioning tool having a pair of handles having operative ends, with one of the ends being attached relative to one of the openings in the plate of FIG. 2 and another of the ends being anchored relative to a bone, showing the tensioning tool pulling the body of the plate in a direction generally away from the legs of the plate to tension the body prior to insertion of a first of the bone screws into a pre-drilled guide hole aligned with one of the screw holes of the plate.
Figure 21:
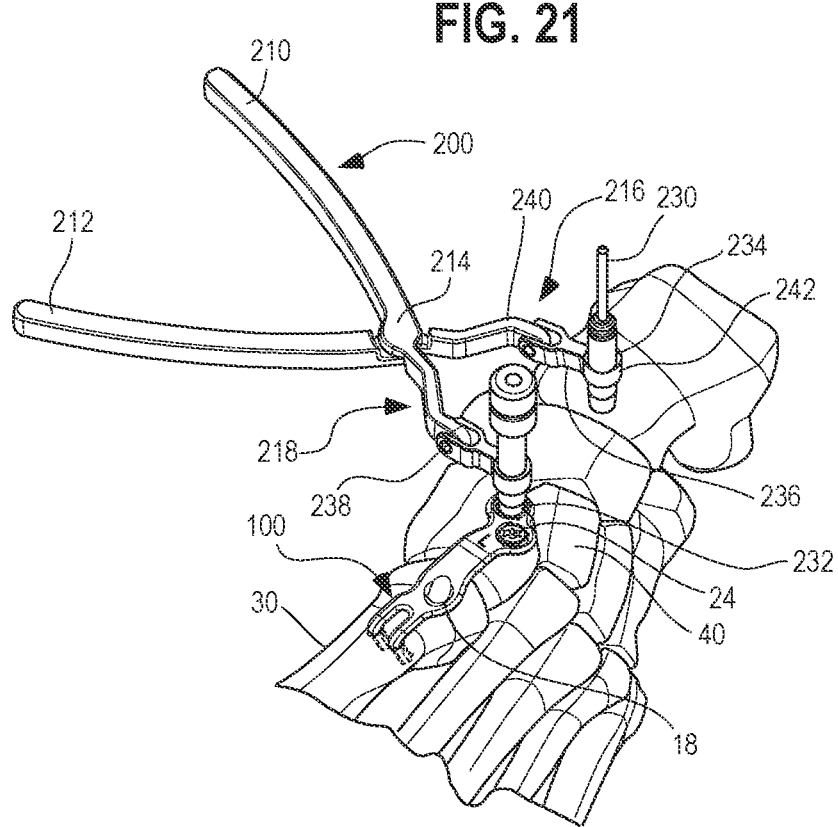
FIG. 21 is another perspective view of the tensioning tool of FIG. 20, showing the first of the bones screws threaded into the pre-drilled guide hole.

A tensioning tool 200 can be used for tensioning the plate 10 during insertion of at least one of the screws. The tensioning tool, an exemplary embodiment of which is shown in FIGS. 20 and 21, can include a pair of arms 210, 212 connected about a pivot 214. One end of the arms on one side of the pivot include handle, and the opposite end of the arms on the other side of the pivot include operating ends 216, 218, details of which will be described further herein. Squeezing the handles together causes the operating ends 216, 218 of the arms 210, 212 to also move together.

A bone anchoring pin 230 can be inserted into a pre-drilled guide hole at a location spaced from the plate 10 and on an opposite side the plate 10 from the legs 20, as shown in FIGS. 20 and 21. A plate pin 232 can have an external thread on its tip such that it can be threadingly engaged with the internal threads of one of the two screw holes, preferably the rearward most screw hole, having internal threads, also as shown in FIGS. 20 and 21. The operating ends of the arms 216, 218 can be identical, and, as best shown in FIG. 21, are configured for attachment relative to the bone anchoring pin 230—either directly or via a cannulated sleeve 234 disposed about the bone anchoring pin 230, as shown in FIGS. 20 and 21—and relative to the plate pin 232—either directly or via a sleeve disposed about the plate pin 232. The operating ends 216, 218 are configured for attachment by having an annular ring 242 that can fit around the pins or sleeves. Optionally, the rings can be pivotably attached relative to adjacent portions of the arms to allow for the handles to be pivotably orientated relative to the operating ends for facilitating positioning and use of the handles during operation of the tensioning tool. The rings can, for example, each be attached to a support 236 terminating in a clevis 238 that is pivotably attached the adjacent portions 240 of the arms 210, 212. When the rings are mounted relative to the pins, squeezing the handles together causes the operating ends of the arms to move together, thereby pulling the plate away from the legs thereof and toward the anchoring pin, thereby tensioning the body of the plate. Optionally, the arms can be locked in the tensioning position, such as by fixing the pivot therebetween or blocking the arms from moving away from each other (such as by using a clamp).

Figure 22:
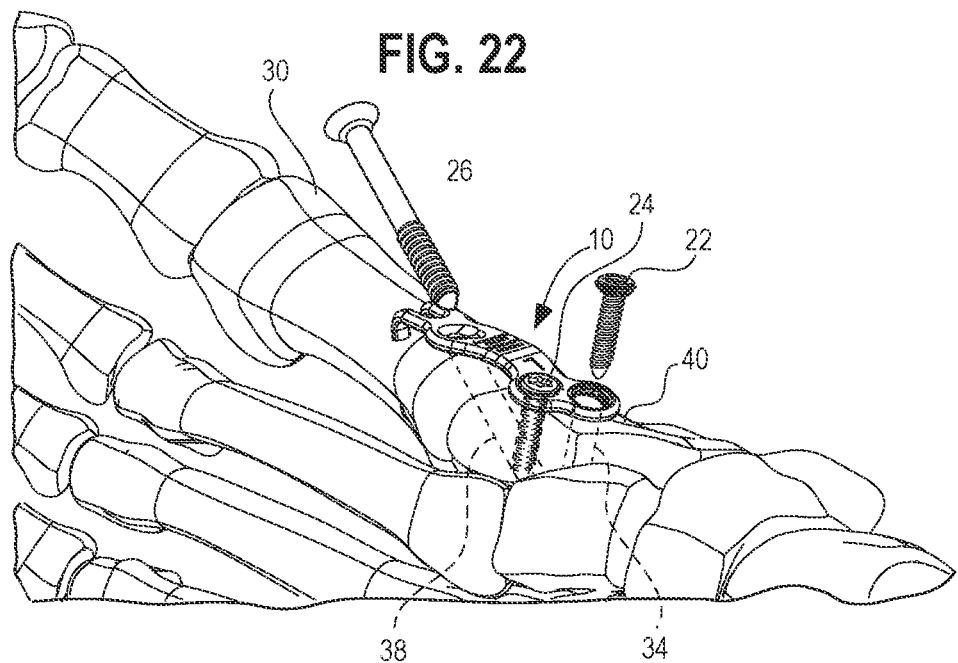
FIG. 22 is a perspective view of the plate of FIG. 2 fusing the first metatarsal and the first proximal phalanx, with the legs of the plate being inserted into the pre-drilled guide holes in the first metatarsal, the first of the bone screws attached to the body of the plate and inserted into pre-drilled guide hole in the first proximal phalanx, and showing predrilled guide holes for a second of the bone screws and the optional bridging screw.
Figure 23:
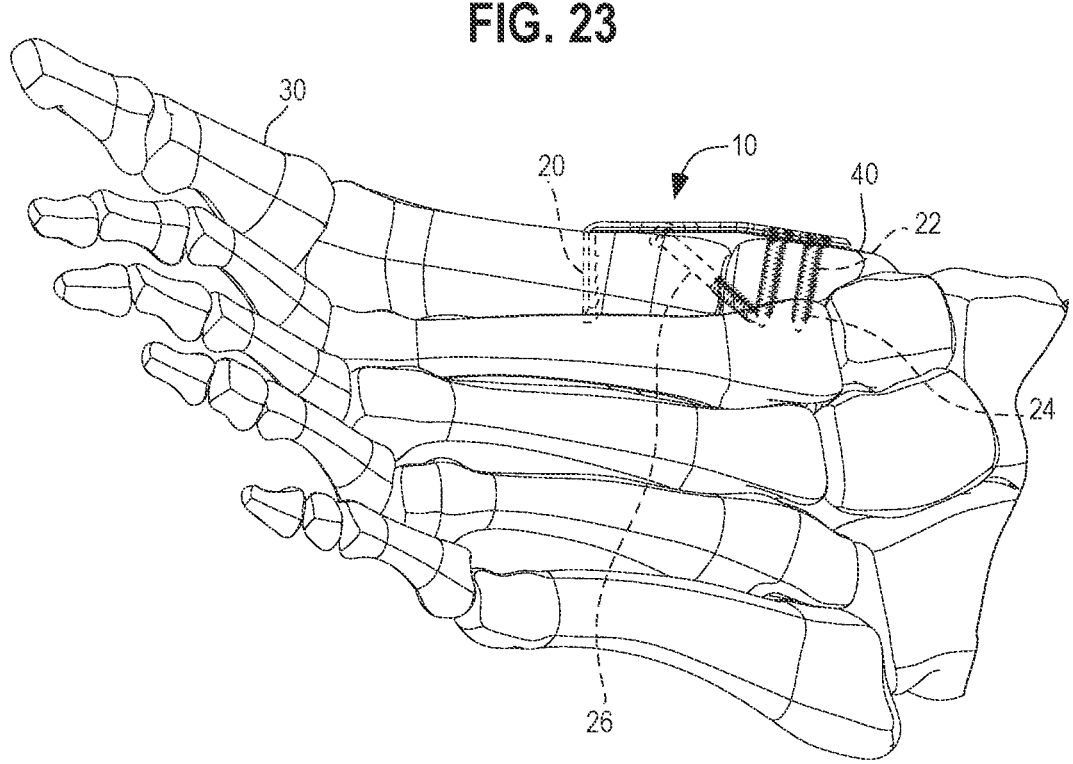
FIG. 23 is a side elevation view of the plate attached to the bones using the legs of the plate, the two screws and the optional bridging screw to fuse the bones together.
Figure 25A:
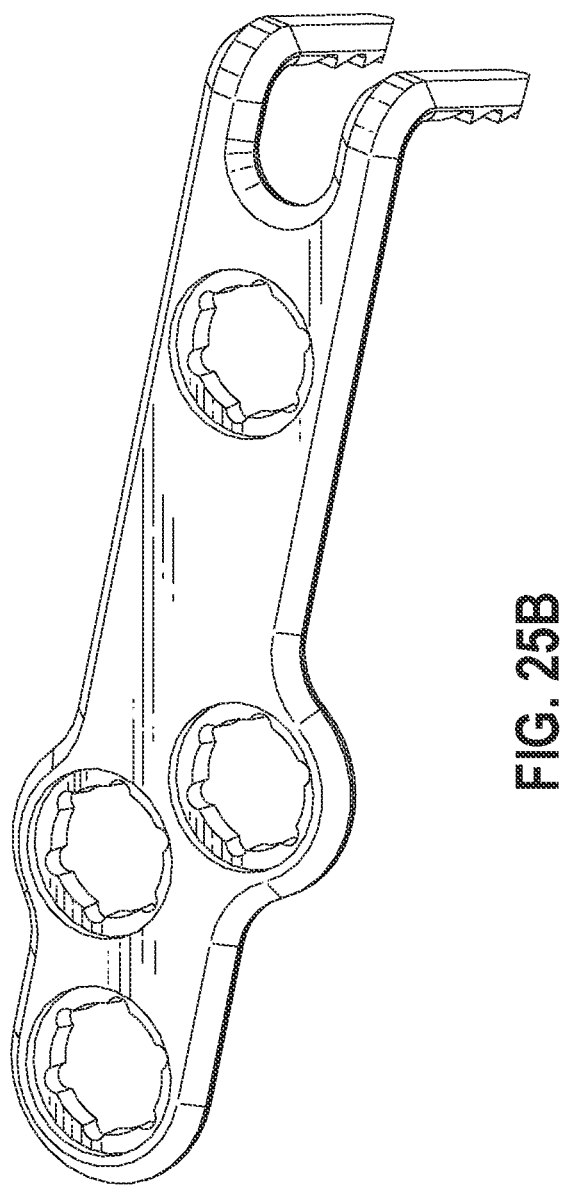
FIG. 25A is a perspective view and FIG. 25B is a side elevation view of a third embodiment of a plate having a body portion with a pair of legs at one thereof and three offset screw holes at an opposite end portion, the pair of legs being at an acute angle relative to the body, and an intermediate fourth screw hole in the body between the legs and the other three screw holes.
Figure 25B:
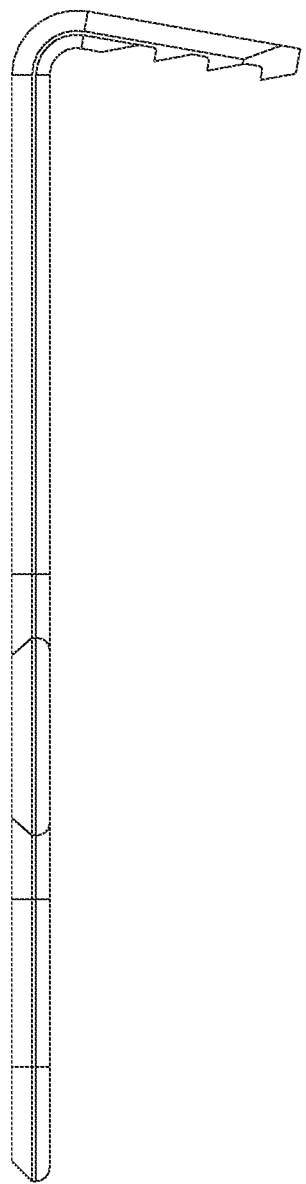

When the plate is under tension, a guide hole 34, such as shown in FIG. 20, can be drilled in the bone underlying the other of the two internally threaded screw holes. A screw can then be threaded into the hole and the head of the screw threadingly engaging with the internal thread of the screw hole, as shown in FIG. 21. Thus installed, the plate is tensioned between the installed screw and the legs. At this point, the tensioning tool 200 can be removed and guide holes for the other two screws can be made in the bones, as shown in FIG. 22. Finally, the other two screws can be inserted through their respective holes, as shown in FIG. 23, to finish the insertion of the plate. Advantageously, the tension in the body of the plate as well as the tension in the legs, which are biased to return from a generally perpendicular orientation to the original acute orientation, individually and together combine to contribute to improved compression of the bones that are being fused together. As mentioned above, the bridging screw is optional. The bridging screw can also be inserted prior to removal of the tensioning tool.

Figure 5:
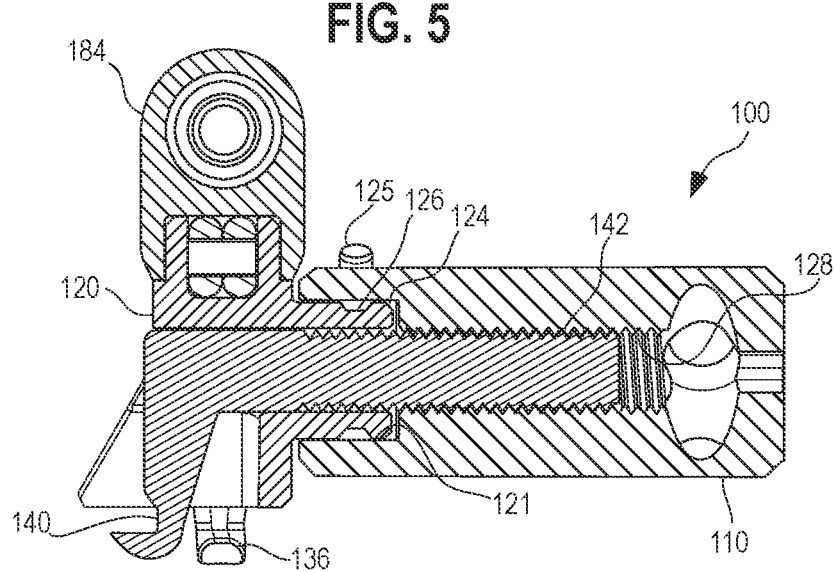
FIG. 5 is a cross-section view of the plate insertion tool of FIG. 1, taken along line V-V of FIG. 4.
Figure 6:
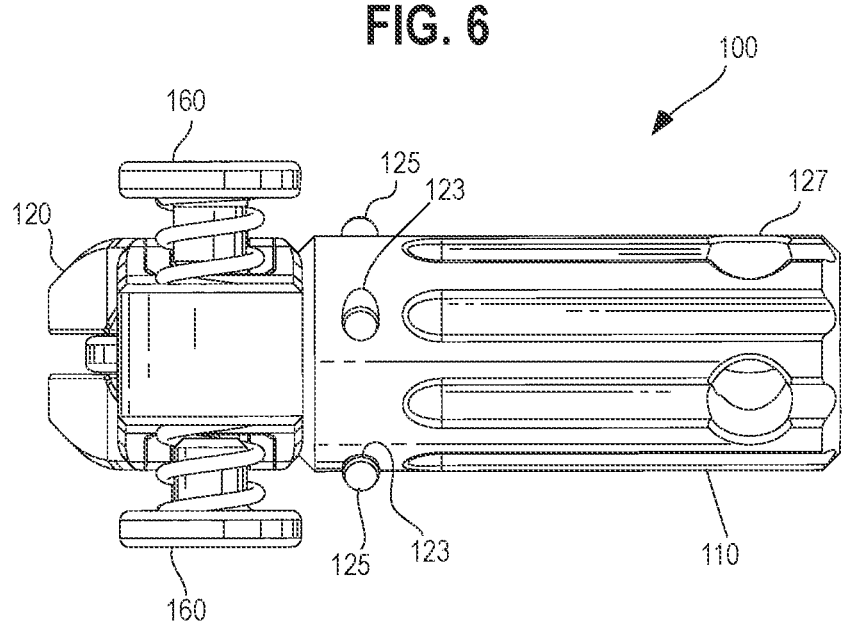
FIG. 6 is a top plan view of the plate insertion tool of FIG. 1.
Figure 7:
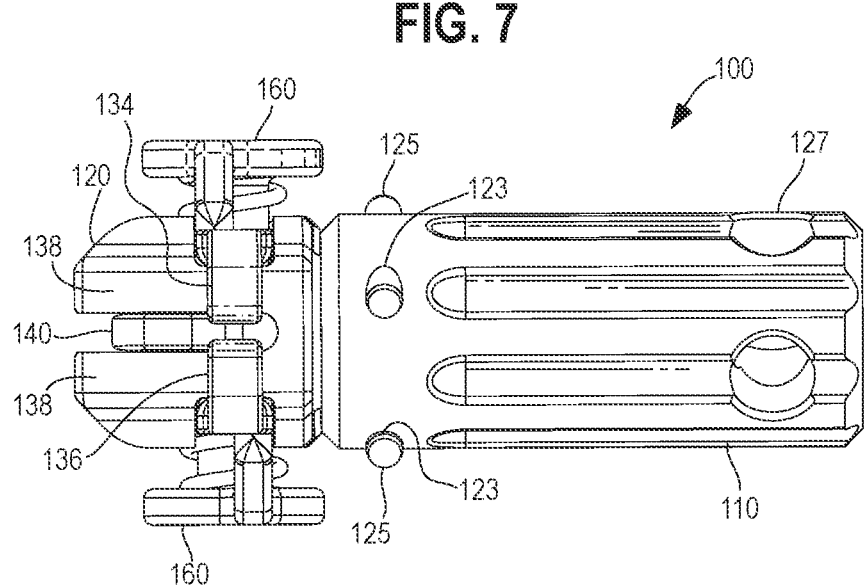
FIG. 7 is a bottom plan view of the plate insertion tool of FIG. 1.

Turning now to details of the plate insertion tool 100, the head 120 includes a rearward-facing annular extension 124 that has a circumferentially-extending groove 126, as shown in FIGS. 5 and 8. The handle 110 has a central threaded bore 128 along a central axis thereof and, at the end facing the head 120, an annular recess 121 for receiving the annular extension 124 of the head 120, as shown in FIG. 8. A pair of transverse through-bores 123 intersect the recess 121 but are spaced from the central threaded bore 128. The transverse through-bores 123 are positioned on the handle 110 such that, when the handle 110 is mounted on the annular extension 124 of the head 120, they are aligned with the circumferentially extending groove 126 of the annular extension 124. When pins 125 are inserted into the through bores 123, the pins 125 allow for rotation of the handle 110 about the annular extension 124 of the head 126, but engagement between the pins 125 and the circumferentially extending groove 126 restrict or prevent axial movement between the head 120 and the handle 110. The handle 110 can include several openings 127 about a rearward portion of its circumference. A tool 129, such as a rod or an end of a driver, can be inserted into one of the openings 127 to provide leverage for rotating the handle 110. Similarly, the rearward end of the handle 110 can include a threaded opening 131 for attachment of a threaded end of a tool, such as a driver, that can used for leverage in rotating the handle 110.

Figure 4:
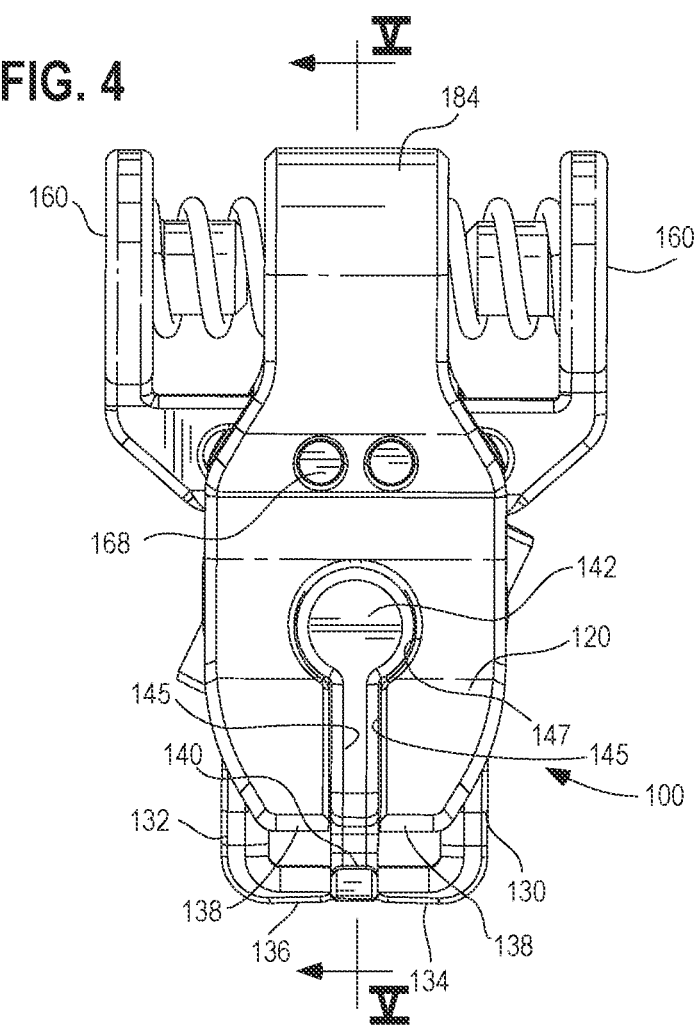
FIG. 4 is a front elevation view of the plate insertion tool of FIG. 1.

The pusher finger 140 is disposed at the end of a threaded shaft 142. The head 120 includes a pair of depending legs 133 with a gap therebetween. The legs 133 have the generally planar bottom surfaces 138, as shown in FIG. 4. The pusher finger 140 is positioned between the legs 133 of the head 120 and beneath the generally planar bottom surfaces 138 of the legs 133, as shown in FIG. 8. The pusher finger 140 has a pair of planar sides 140 that can slide between matching generally planar, facing sides 145 of the legs 133. The shaft 142 also extends between the legs 133, and can slide between along an arcuate surface 147 that spans between the legs 133. The shaft 142 extends rearwardly from the pusher finger 140 and through the annular extension 124 and into the threaded bore 128 of the handle 110. Engagement between the planar sides of the pusher finger 144 and the planar, facing sides 145 of the legs 133 prevents rotation of the shaft 142. However, rotation of the handle 110—which is axially fixed relative to the head 120—forces the shaft 142, and thus the pusher finger 142, to slide forward or backward relative to the head 120. In this manner, the handle 110 can be rotated to move the pusher finger 140 between its extended and retracted positions.

Figure 9:
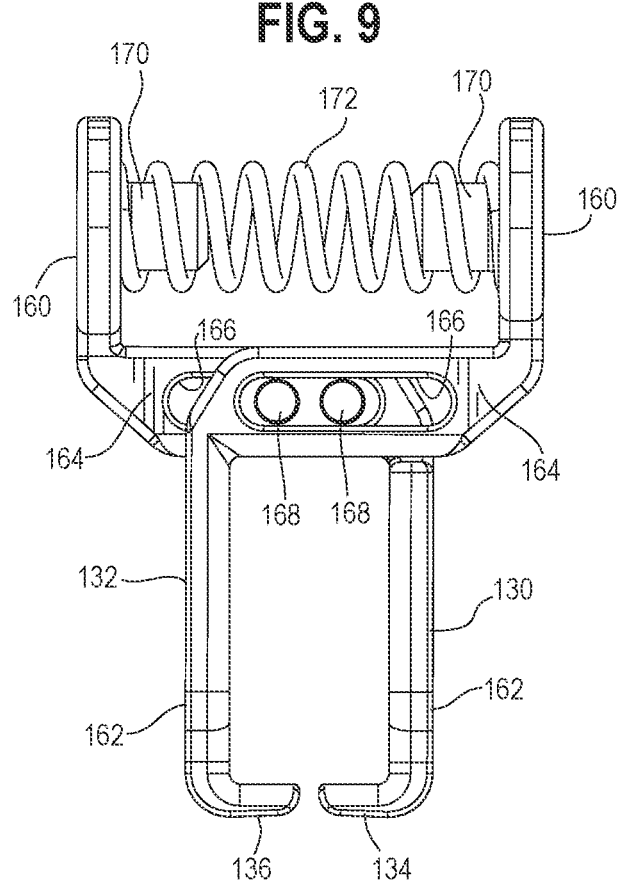
FIG. 9 is a front elevation view of the arms of the plate insertion tool of FIG. 1, showing the arms being slid together such that inwardly extending fingers at the ends of the arms are in a clamping position, with a spring disposed between actuators at the opposite ends of the arms from the inwardly extending fingers and biasing the actuators away from each other to slide the inwardly extending fingers toward each other.
Figure 10:
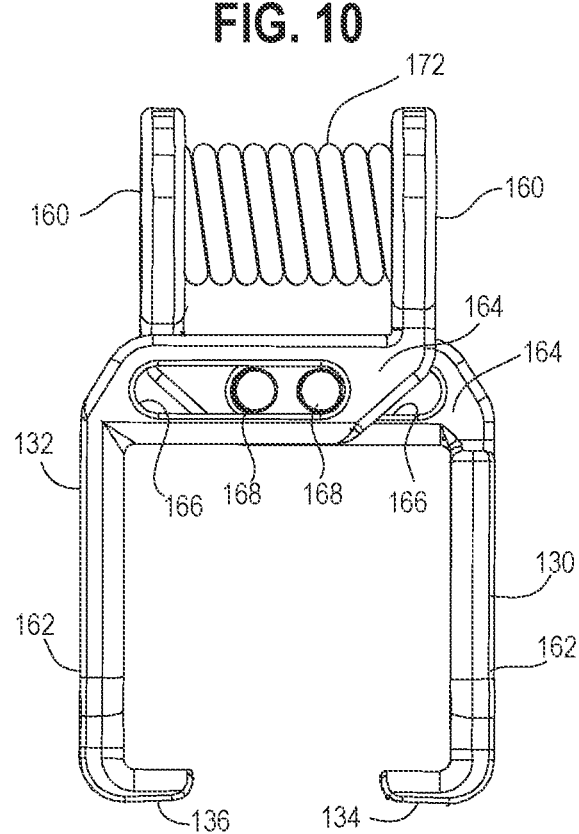
FIG. 10 is a front elevation view of the arms of the plate insertion tool of FIG. 1, showing the arms being slid away from each other such that the inwardly extending fingers at the ends of the arms are in an open position, with the spring disposed between actuators being compressed and the actuators being closer to each other as compared to in FIG. 9.
Figure 11:
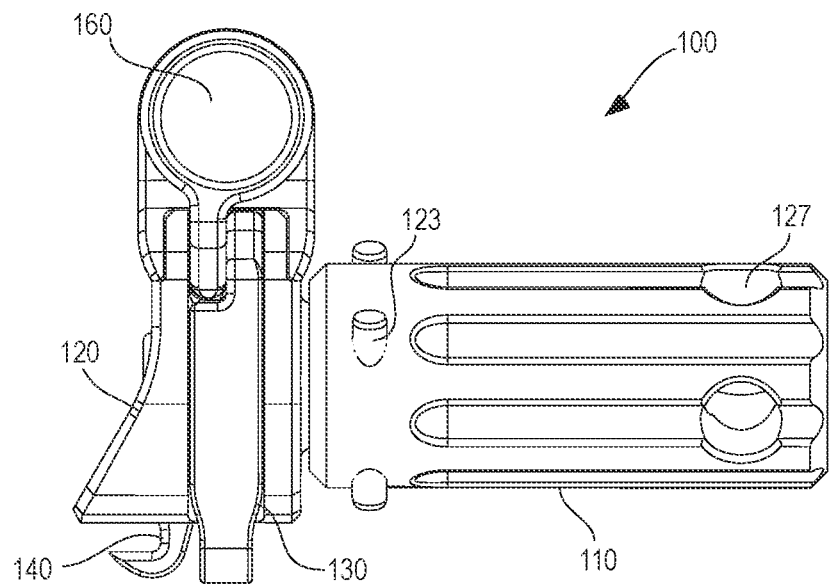
FIG. 11 is a left side elevation view of the plate insertion tool of FIG. 1, showing the pusher finger in a retracted position.
Figure 12:
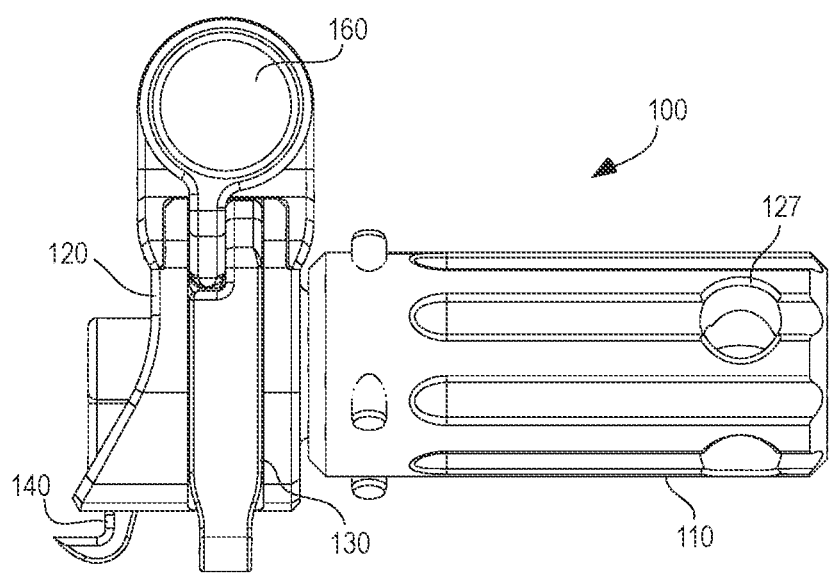
FIG. 12 is a left side elevation view of the plate insertion tool of FIG. 1, showing the pusher finger in an extended position.

As mentioned above, each of the arms 130, 132 of the plate insertion tool 100 includes an inwardly extending finger 134, 136. The arms 130, 132 are identical, so like numbers will be used for like parts. The arms 130, 132 each also include an actuator 160 at an opposite end thereof. The actuator 160 can be in the form of a disc or other shape that can be pushed by a surgeon or other user. The arms 130, 132 each include a lower leg 162 that is generally perpendicular to the inwardly extending finger 134, 136, a transverse leg 164 that is generally perpendicular to the lower leg 162 (and thus generally parallel with the inwardly extending finger 134, 136), and, at an opposite end of the transverse leg 164 from the lower leg 162, the actuator 160 (which can be generally upstanding, and generally perpendicular to the transverse leg), as shown in FIGS. 8-10. Although the arms 130, 132 are identical, they abut each other on different sides, as shown in FIGS. 9 and 10.

The transverse legs of the arms each include an obround opening 166. A pair of parallel, spaced arm pins 168 extend through the obround openings, as shown in FIGS. 9 and 10. The pins are fixed to the head, as will be explained in further detail. The pins and the obround openings are shaped such that the arms can only slide toward or away from each other. The actuators include an inward side that includes a stud 170 for supporting a compression spring 172 between the studs, and thus, the actuators, when assembled. The spring biases the actuators away from each other, which in turn causes the inwardly extending fingers to be biased toward each other into the clamping position, which is shown in FIG. 9. When the actuators are squeezed together against the biasing force of the spring, the arms are constrained by the fixed pins so that the opposite ends of the arms, with the inwardly extending fingers, slide away from each other into the open position, which is shown in FIG. 10. Once the actuators are no longer squeezed together, the bias of the spring then moves the arms so that the inwardly extending fingers are in the clamping position.

The head includes a pair of upwardly extending flanges 180 with a gap therebetween, as shown in FIG. 8. The transverse legs of the arms are partially disposed between the flanges. The flanges each include two apertures 182, and the opposing apertures of the flanges are aligned to receive the arm pins. When the transverse legs are partially disposed in the gap between the flanges, the pins extend through the obround openings in the transverse legs. The transverse legs, and thus the arms, can slide relative to each other but engagement of the fixed pins and the obround openings limits the extent of sliding. An upper bracket 184, shown in FIG. 8, has a pair of depending flanges 186 with opposing apertures 188. The upper bracket can engage with the head, with the flanges of the upper bracket disposed outwardly from the pair of upwardly extending flanges of the head. The apertures of the depending flange of the upper bracket can align with the aperture of the upwardly extending flanges of the head such that the same pins can be used to secure the flanges together, and thus the upper bracket to the head. The upper bracket can also include a through opening 189, parallel to the depending flanges, for receiving a central part of the spring.

Alternative Plates

There are many different types of configurations of the plates that can be suitable for different fusion and other procedures. As mentioned above, the plates can be compression plates that are formed of a shape-memory material, such as nitinol. In addition to the first exemplary embodiment of a plate illustrated in FIGS. 2 and 3, twenty-four alterative embodiments are illustrated in FIGS. 24A-47B. The plates each have at least one screw hole at one end portion of a body and a pair of depending legs at another end of the body. The pair of legs are at an acute angle relative to the extension. In some embodiments, the legs are side by side with a shoulder therebetween; in other embodiments, the legs are in-line and depend from a linear extension of the body. The plate insertion tool and/or the methods described herein can be used for tensioning the pair of legs.

Some plates have two screw holes and others three screw holes. Optionally, the screw holes can be configured with internal threads for engaging with external threads on the heads of the screws. The screw holes can be in-line, e.g., lying along a center-line of the body. The screw holes can alternatively be offset relative to each other. In yet another alternative, the screw holes can be arranged transverse, e.g., in a line transverse to a center-line of the body, in a T-shaped body, for example.

Some of the plates also have an intermediate screw hole. The intermediate screw hole, if present, can optionally be used for a bridging screw that passes through one bone and at least partially into another. The portion of the body surrounding the intermediate screw hole can include a contour that cooperates with a contour of the underside of the bridging screw to stabilize the head of the bridging screw against the body. Instead of a bridging screw, the other type of screw and screw hole can be used.

The geometry of the plates can be tailored for different indications. By way of non-limiting examples, the plates of FIGS. 24A-25B and 38A-47B can be used for arthrodesis of the first metatarsophalangeal joint (MTP) or 1st (Lapidus), 2nd, 3rd, 4th, and 5th tarsometatarsal (TMT) fusions, various fracture fixation, or Lisfranc fusion or stabilization.

The plates of FIGS. 26A-27B and 34A-37B can be used for arthrodesis of the first metatarsophalangeal joint (MTP) or 1st (Lapidus), 2nd, 3rd, 4th, and 5th tarsometatarsal (TMT) fusions or various fracture fixation. The plates of FIGS. 28A-31B can be used for talo-navicular (TN) fusion, calcaneo-cubioid (CC) fusion, Lapidus fusion, or Navicular-cuneiform (NC) fusion. The plates of FIGS. 33A-34B can be used for Akin osteotomy, 1st, 2nd, 3rd, 4th, and TMT fusions, intercuneiform fusions, Jones or avulsion fractures of the 5th metatarsal, or various fractures.

Turning now to more specific details of the various embodiments of the plates, FIGS. 24A and 24B show a second embodiment of a plate having a body portion with a pair of legs—arranged side by side—at one thereof and three offset screw holes at an opposite end portion, the pair of legs being at an acute angle relative to the body. Optionally, an intermediate fourth screw hole can be provided in the body between the legs and the other three screw holes, as depicted in the third embodiment of FIGS. 25A and 25B.

Figure 26A:
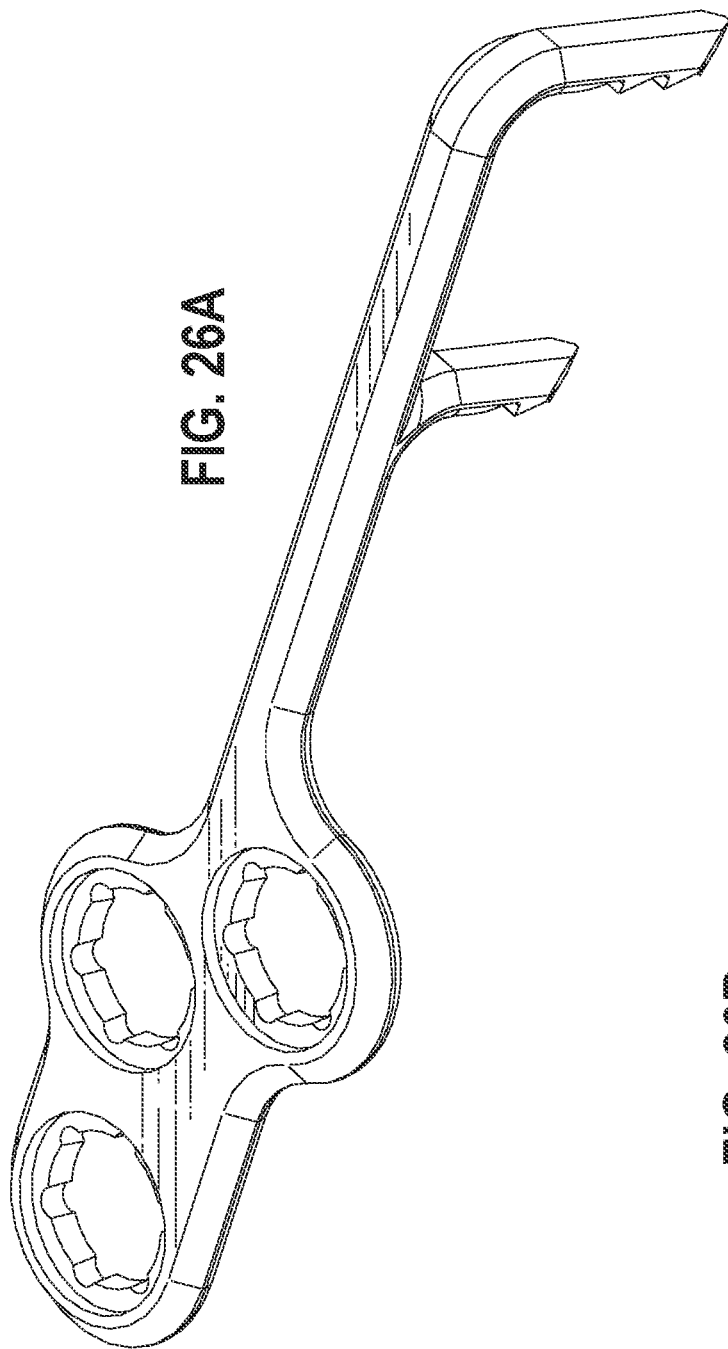
FIG. 26A is a perspective view and FIG. 26B is a side elevation view of a fourth embodiment of a plate having a pair of legs depending from a linear extension and arranged in-line and three offset screw holes in a body at an opposite end of the extension from the legs, the pair of legs each being at an acute angle relative to the extension.
Figure 26B:
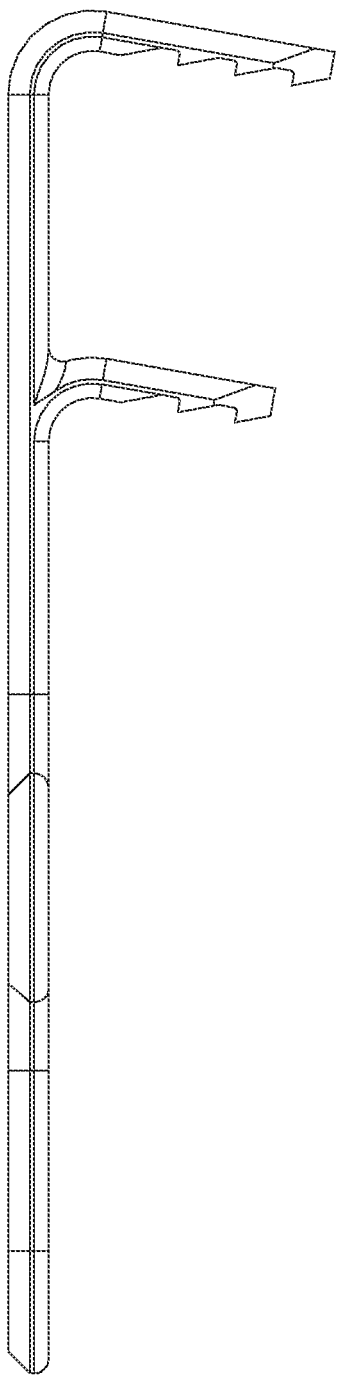
Figure 27A:
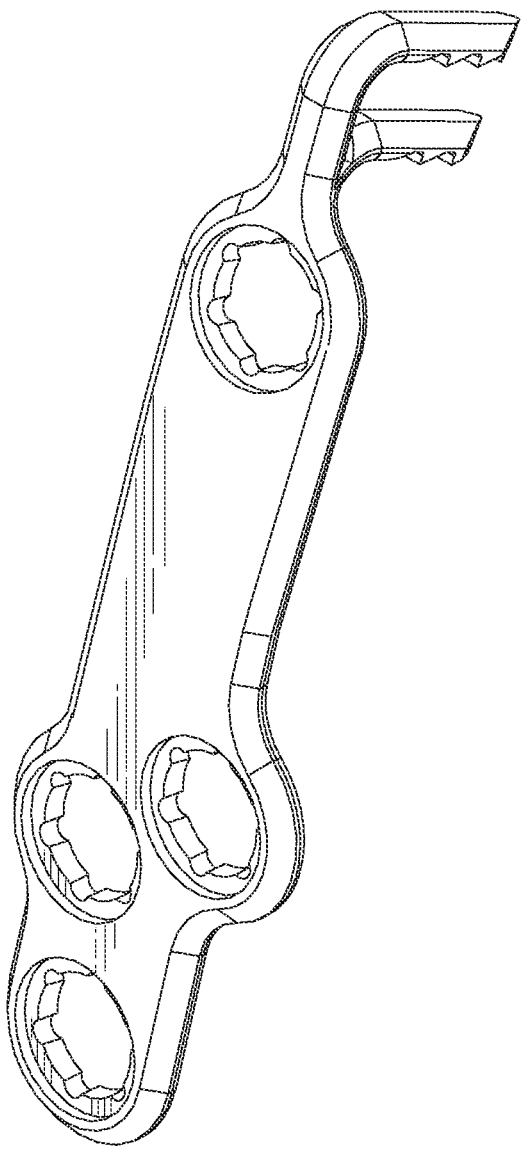
FIG. 27A is a perspective view and FIG. 27B is a side elevation view of a fifth embodiment of a plate having a pair of legs depending from a linear extension and arranged in-line and three offset screw holes in a body at an opposite end of the extension from the legs, the pair of legs each being at an acute angle relative to the extension, and an intermediate fourth screw hole in the body between the extension and the other three screw holes.
Figure 27B:
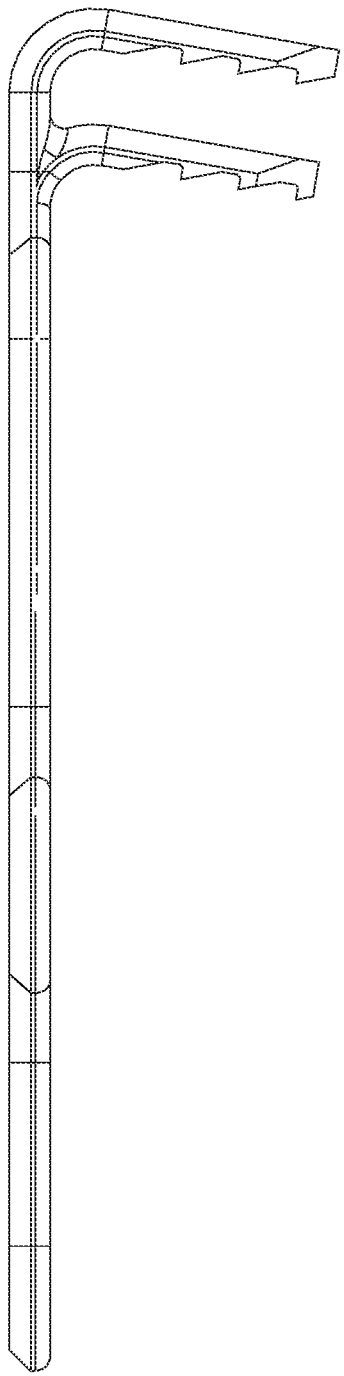

FIGS. 26A and 26B show a fourth embodiment of a plate having a pair of legs depending from a linear extension and arranged in-line and three offset screw holes in a body at an opposite end of the extension from the legs, the pair of legs each being at an acute angle relative to the extension. Optionally, an intermediate fourth screw hole can be provided in the body between the legs and the other three screw holes, as depicted in the fifth embodiment of FIGS. 27A and 27B.

FIGS. 28A and 28B show a sixth embodiment of a plate having a body portion with a pair of legs at one thereof and two transverse screw holes in an inclined, flared end portion of the body, the pair of legs being at an acute angle relative to the body. Optionally, an intermediate third screw hole can be provided in the body between the legs and the inclined, flared end portion of the body, as depicted in the seventh embodiment of FIGS. 29A and 29B.

Figure 30A:
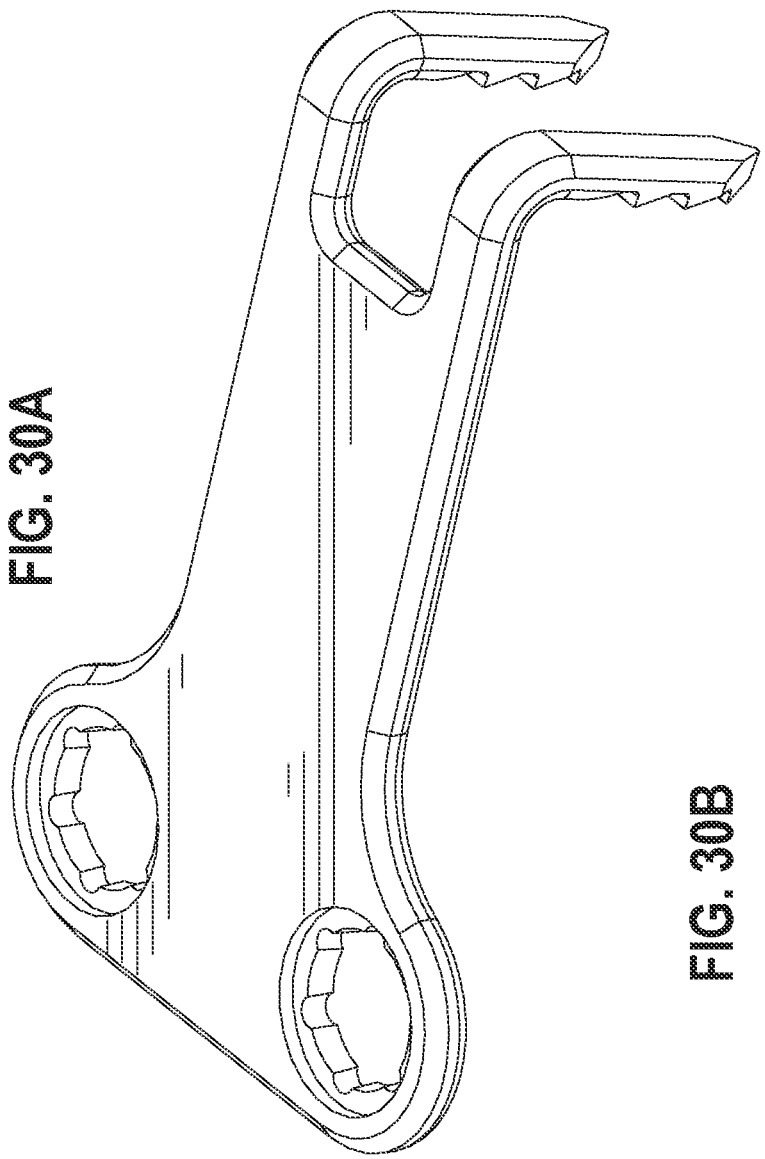
FIG. 30A is a perspective view and FIG. 30B is a side elevation view of an eighth embodiment of a plate having a body portion with a pair of legs at one thereof and two transverse screw holes in a flared end portion of the body, the pair of legs being at an acute angle relative to the body.
Figure 30B:
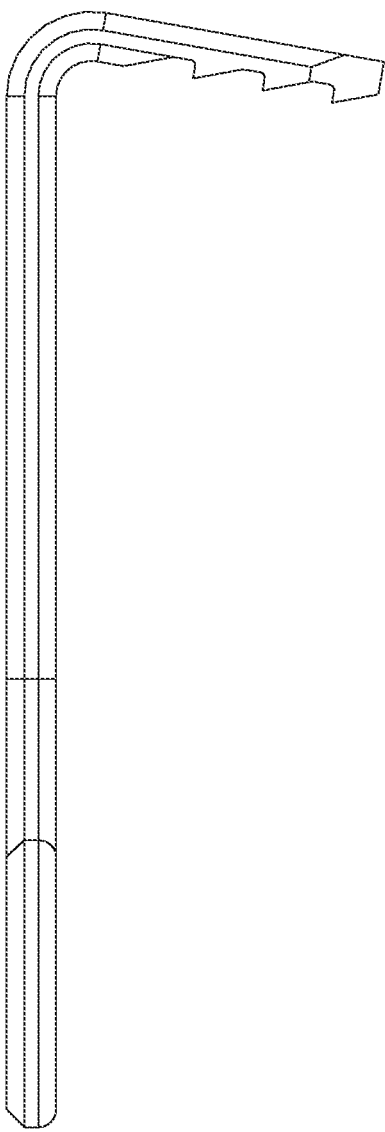

FIGS. 30A and 30B show an eighth embodiment of a plate having a body portion with a pair of legs at one thereof and two transverse screw holes in a flared end portion of the body, the pair of legs being at an acute angle relative to the body. Optionally, an intermediate third screw hole can be formed in the body between the legs and the flared end portion of the body, as depicted in the ninth embodiment of FIGS. 31A and 31B.

Figure 32A:
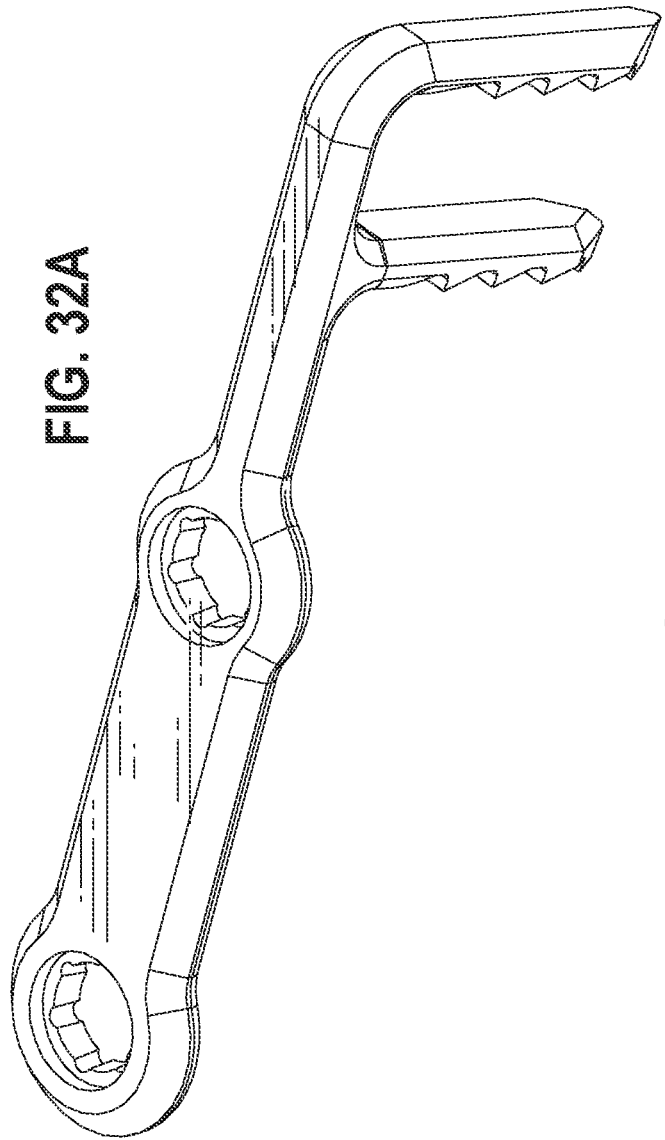
FIG. 32A is a perspective view and FIG. 32B is a side elevation view of a tenth embodiment of a plate having a pair of legs depending from a linear extension and arranged in-line and two in-line screw holes in a body at an opposite end of the extension from the legs, the pair of legs each being at an acute angle relative to the extension.
Figure 32B:
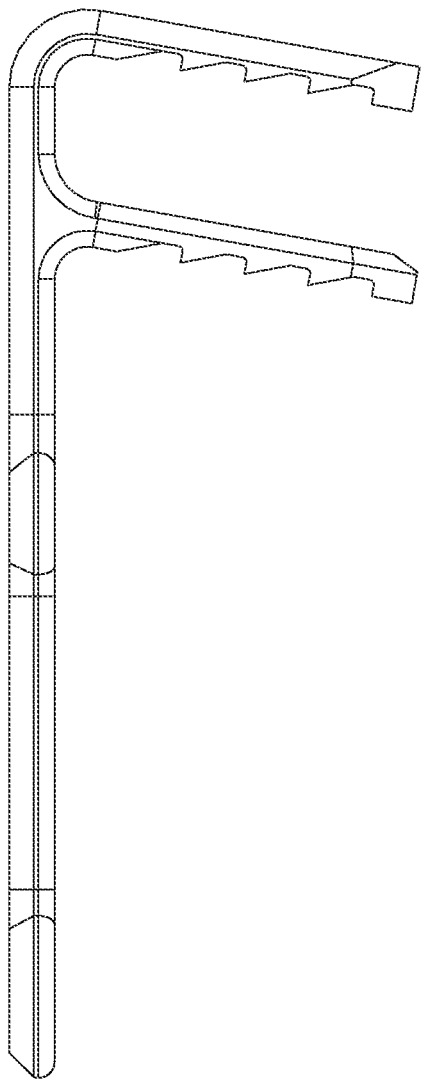

FIGS. 32A and 32B show a tenth embodiment of a plate having a pair of legs depending from a linear extension and arranged in-line and two in-line screw holes in a body at an opposite end of the extension from the legs, the pair of legs each being at an acute angle relative to the extension.

Figure 33A:
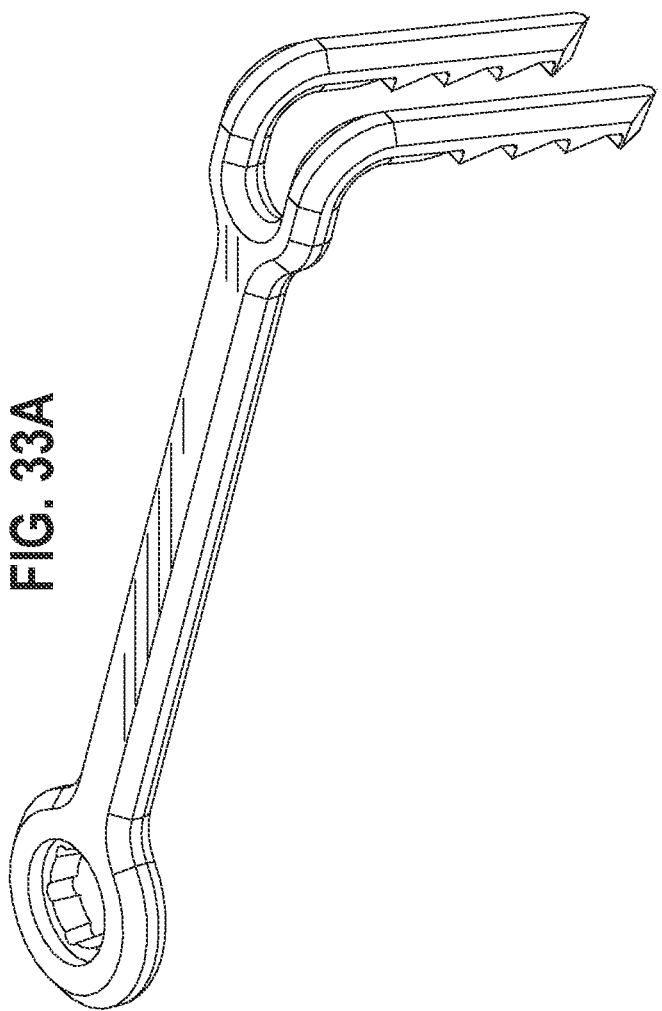
FIG. 33A is a perspective view and FIG. 33B is a side elevation view of an eleventh embodiment of a plate having a pair of legs depending from a linear extension and a screw hole at an opposite end of the extension from the legs, the pair of legs each being at an acute angle relative to the extension.
Figure 33B:
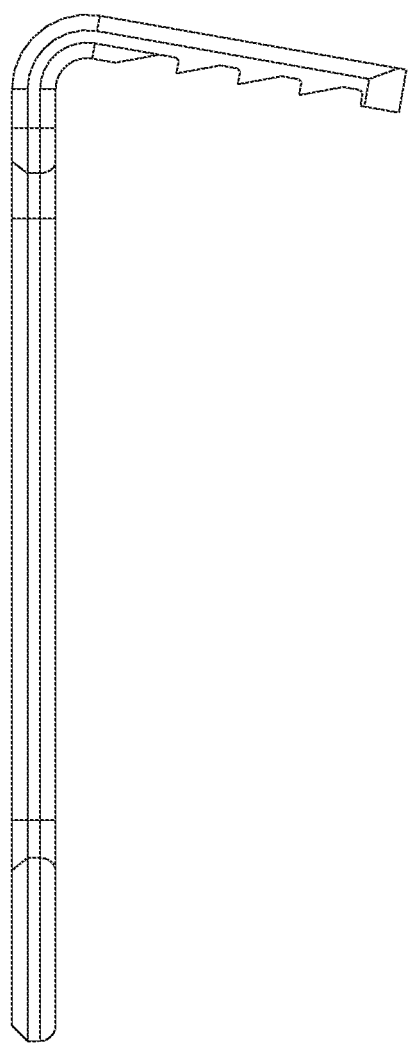
Figure 34A:
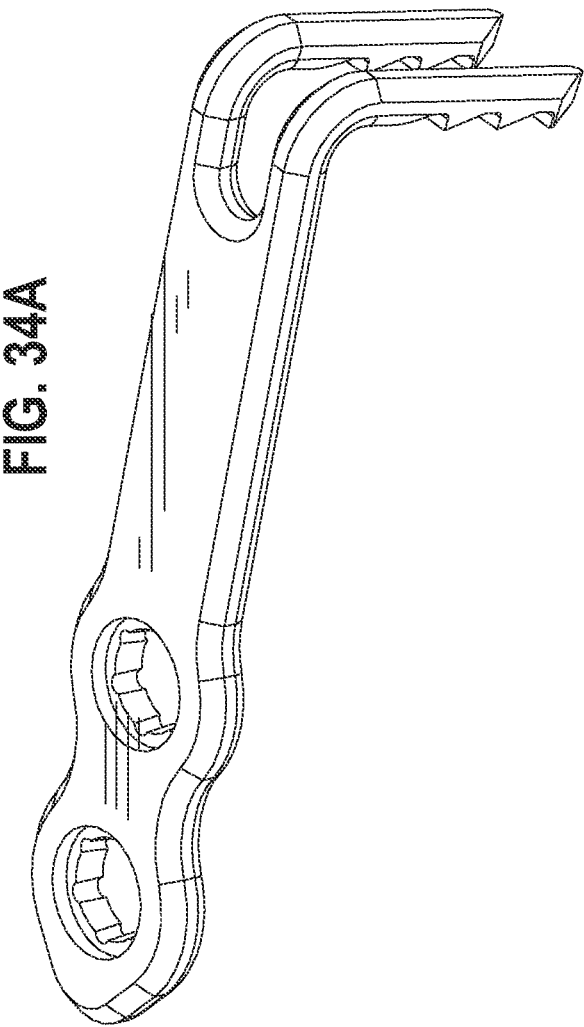
FIG. 34A is a perspective view and FIG. 34B is a side elevation view of a twelfth embodiment of a plate having a body portion with a pair of legs at one thereof and two in-line screw holes at an opposite end portion, the pair of legs being at an acute angle relative to the body.
Figure 34B:
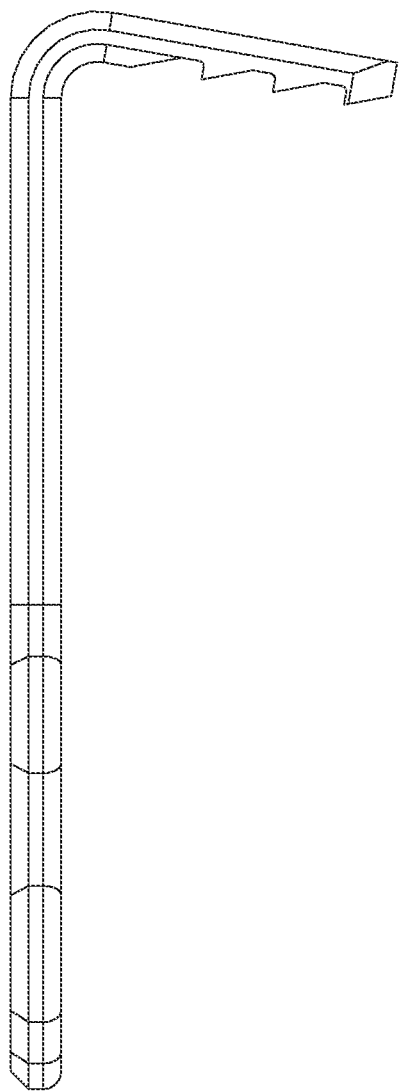

FIGS. 33A and 33B show an eleventh embodiment of a plate having a pair of legs depending from a linear extension and a screw hole at an opposite end of the extension from the legs, the pair of legs each being at an acute angle relative to the extension.

Figure 35A:
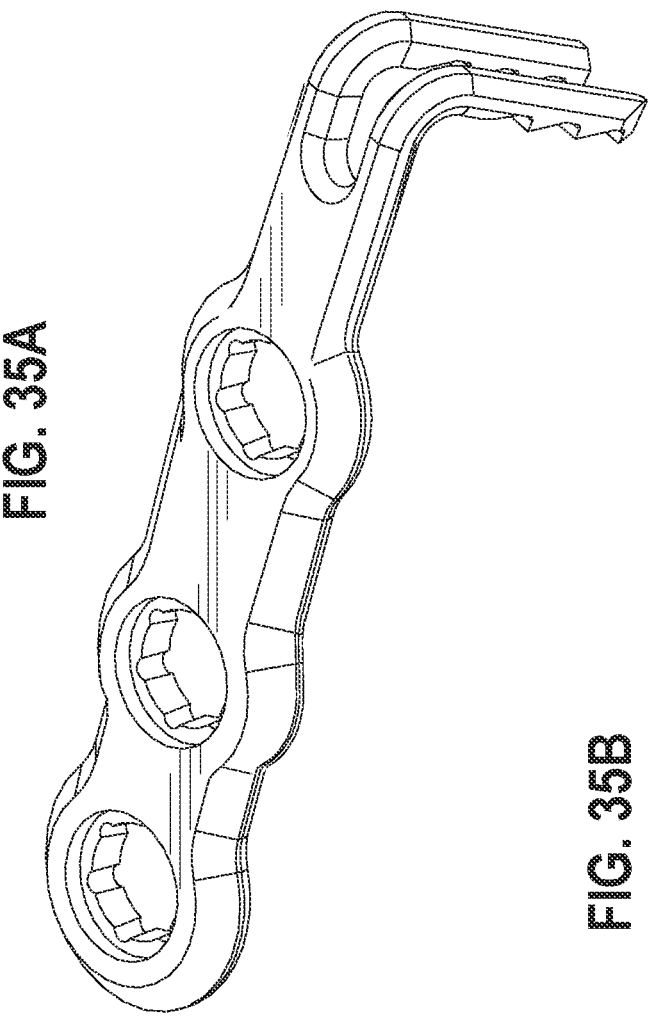
FIG. 35A is a perspective view and FIG. 35B is a side elevation view of a thirteenth embodiment of a plate having a body portion with a pair of legs at one thereof and two in-line screw holes at an opposite end portion, the pair of legs being at an acute angle relative to the body, and an intermediate third screw hole in the body between the legs and the other two screw holes.
Figure 35B:
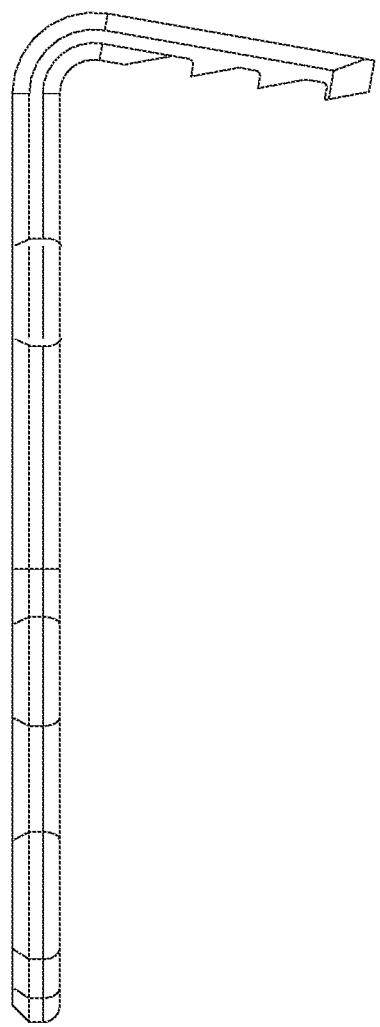

FIGS. 35A and 35B show a twelfth embodiment of a plate having a body portion with a pair of legs at one thereof and two in-line screw holes at an opposite end portion, the pair of legs being at an acute angle relative to the body. Optionally, an intermediate third screw hole can be formed in the body between the legs and the other two screw holes, as depicted in the thirteenth embodiment of FIGS. 35A and 35B.

FIGS. 36A and 36B show a fourteenth embodiment of a plate having a pair of legs depending from a linear extension and arranged in-line and two in-line screw holes in a body at an opposite end of the extension from the legs, the pair of legs each being at an acute angle relative to the extension. Optionally, an intermediate third screw hole can be provided in the body between the extension and the other two screw holes, as in the fifteenth embodiment shown in FIGS. 37A and 37B.

Figure 38A:
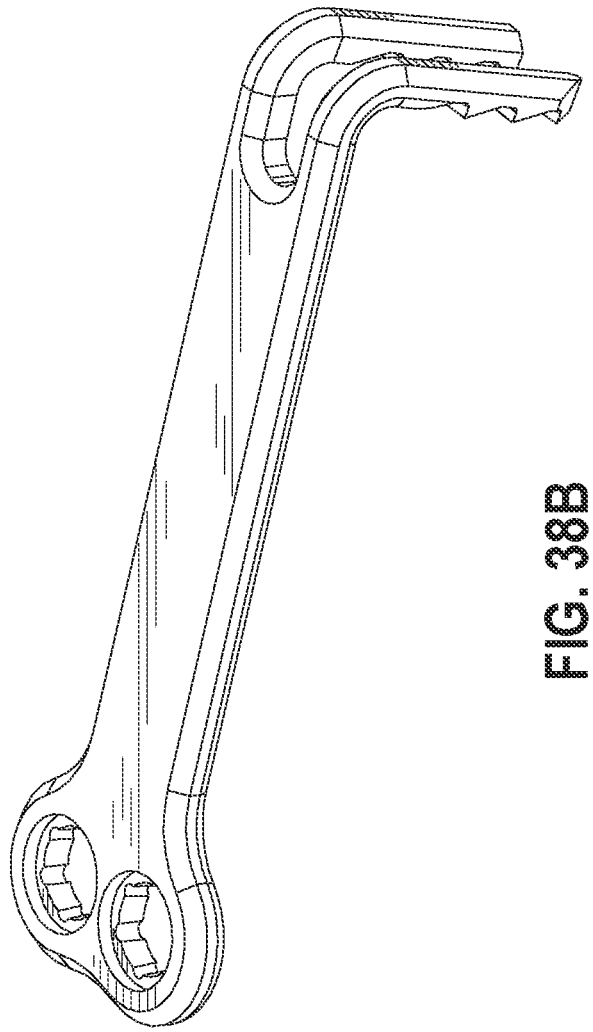
FIG. 38A is a perspective view and FIG. 38B is a side elevation view of a sixteenth embodiment of a plate having a body portion with a pair of legs at one thereof and two transverse screw holes in a flared end portion of the body, the pair of legs being at an acute angle relative to the body.
Figure 38B:
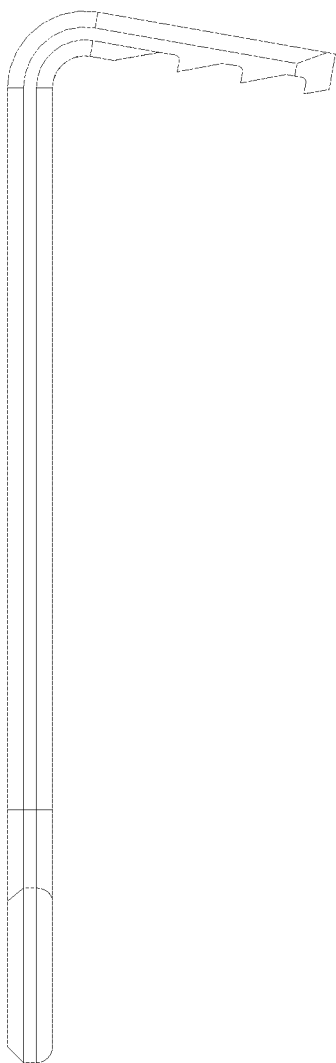
Figure 39A:
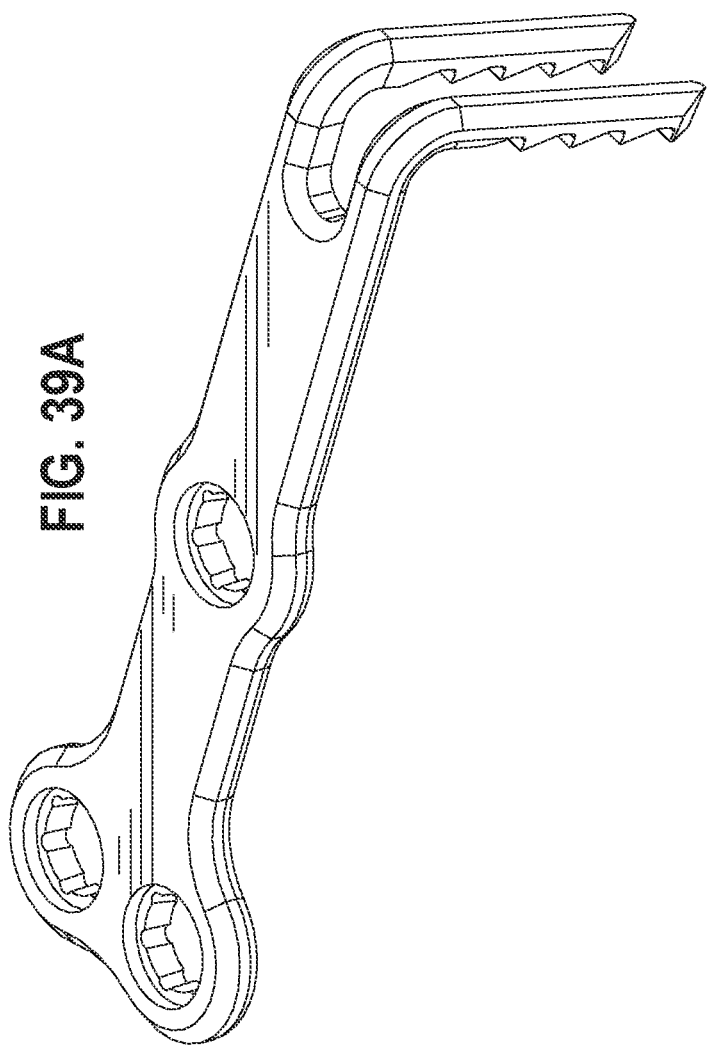
FIG. 39A is a perspective view and FIG. 39B is a side elevation view of a seventeenth embodiment of a plate having a body portion with a pair of legs at one thereof and two transverse screw holes in a flared end portion of the body, the pair of legs being at an acute angle relative to the body, and an intermediate third screw hole in the body between the legs and the flared end portion of the body.
Figure 39B:
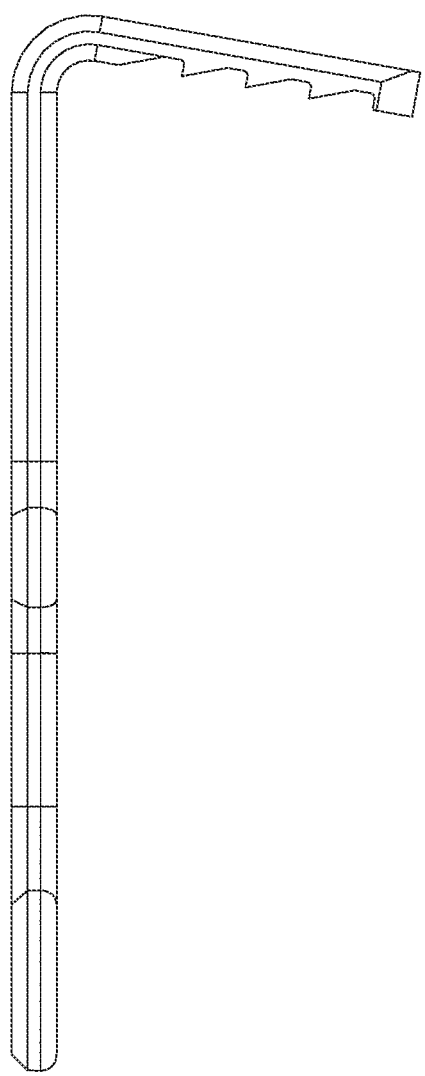

FIGS. 38A and 38B show a sixteenth embodiment of a plate having a body portion with a pair of legs at one thereof and two transverse screw holes in a flared end portion of the body, the pair of legs being at an acute angle relative to the body. As shown in FIGS. 39A and 39B, optionally an intermediate third screw hole can be formed in the body between the legs and the flared end portion of the body.

FIGS. 40A and 40B show an eighteenth embodiment of a plate having a pair of legs depending from a linear extension and arranged in-line and two transverse screw holes in a body at an opposite end of the extension from the legs, the pair of legs each being at an acute angle relative to the extension. Optionally, an intermediate third screw hole can be formed in the body between the extension and the other two screw holes, as in the nineteenth embodiment shown in FIGS. 41A and 41B.

Figure 42A:
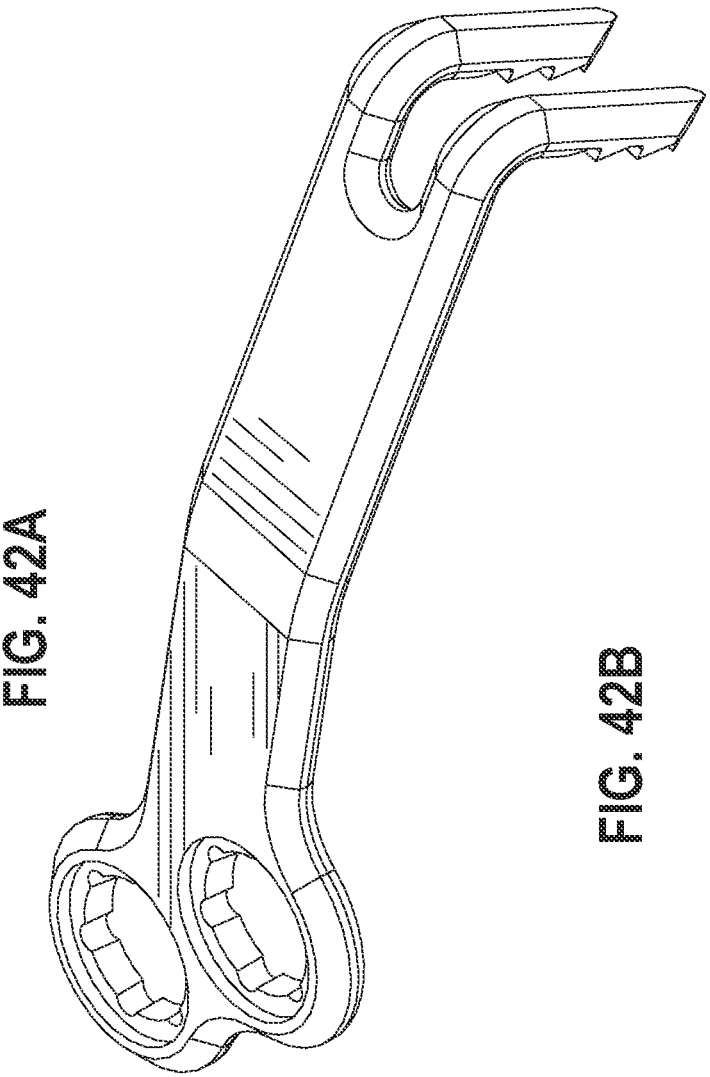
FIG. 42A is a perspective view and FIG. 42B is a side elevation view of a twentieth embodiment of a plate having a body portion with a pair of legs at one thereof and two offset screw holes in an inclined end portion of the body, the pair of legs being at an acute angle relative to the body.
Figure 42B:
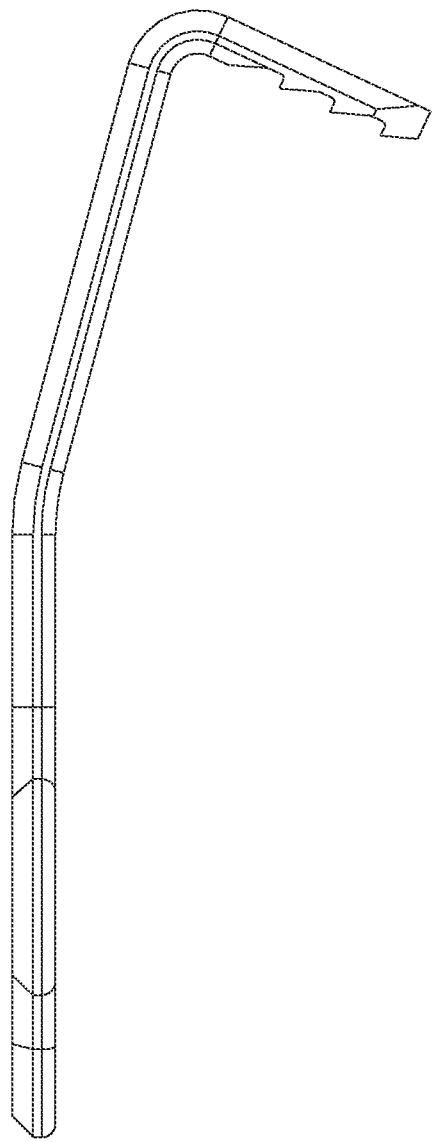
Figure 43A:
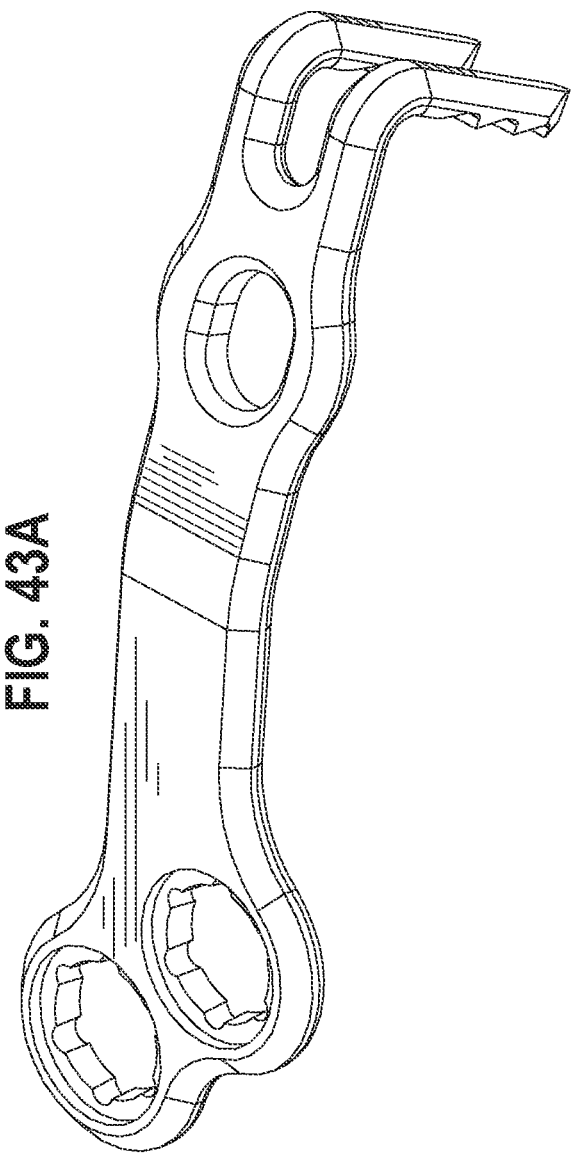
FIG. 43A is a perspective view and FIG. 43B is a side elevation view of a twenty-first embodiment of a plate having a body portion with a pair of legs at one thereof and two offset screw holes in an inclined end portion of the body, the pair of legs being at an acute angle relative to the body, and an intermediate third screw hole in the body between the legs and the inclined end portion of the body.
Figure 43B:
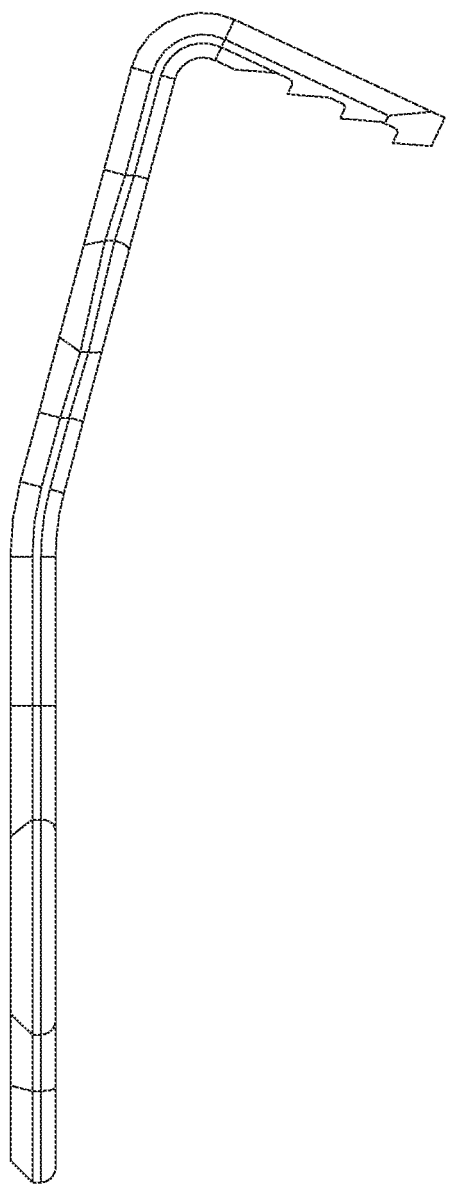
Figures 45A, 45B:
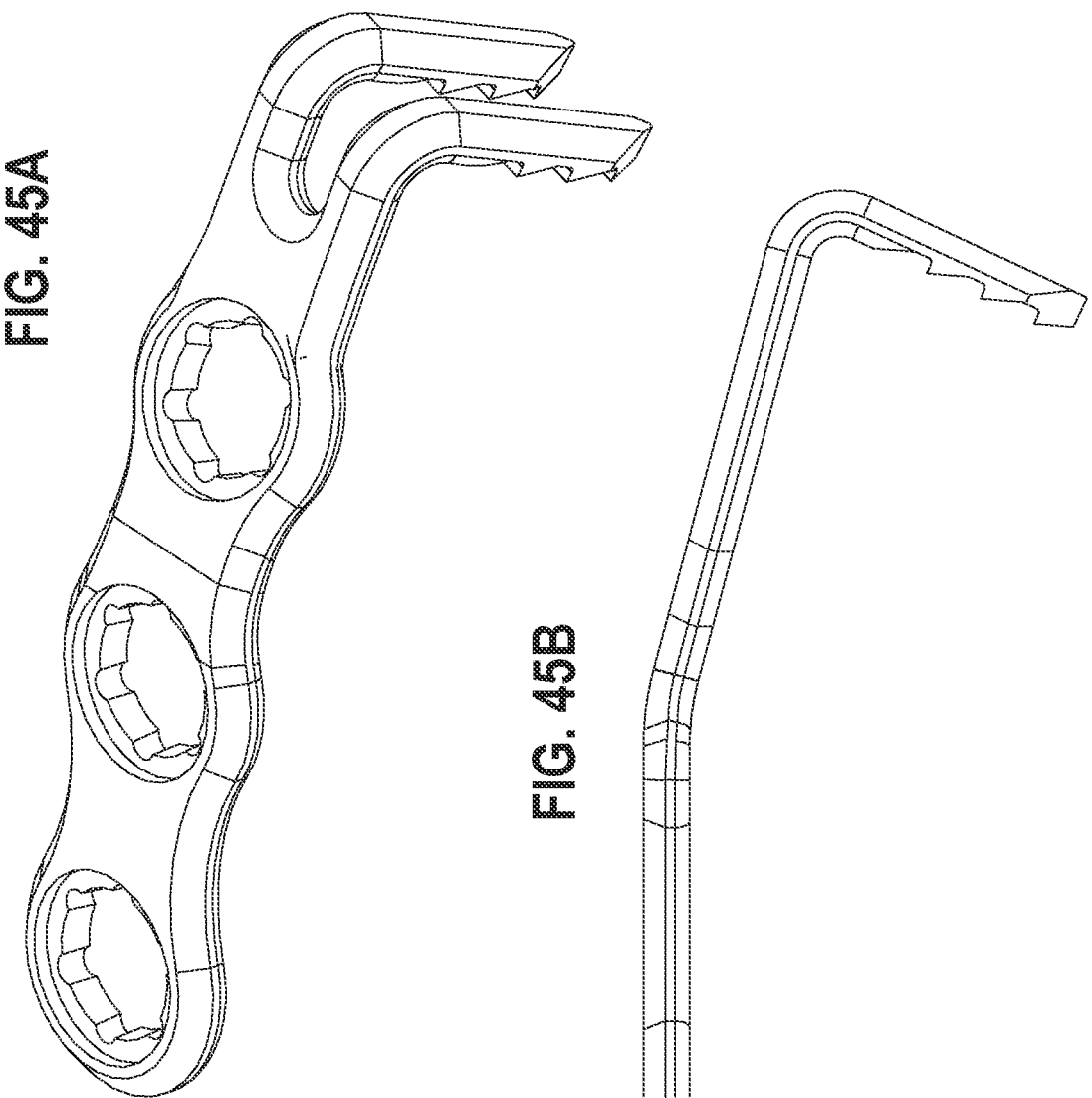
FIG. 45A is a perspective view and FIG. 45B is a side elevation view of a twenty-third embodiment of a plate having a body portion with a pair of legs at one thereof and two in-line screw holes in an inclined end portion of the body, the pair of legs being at an acute angle relative to the body, and an intermediate third screw hole in the body between the legs and the inclined end portion of the body.
Figure 47A:
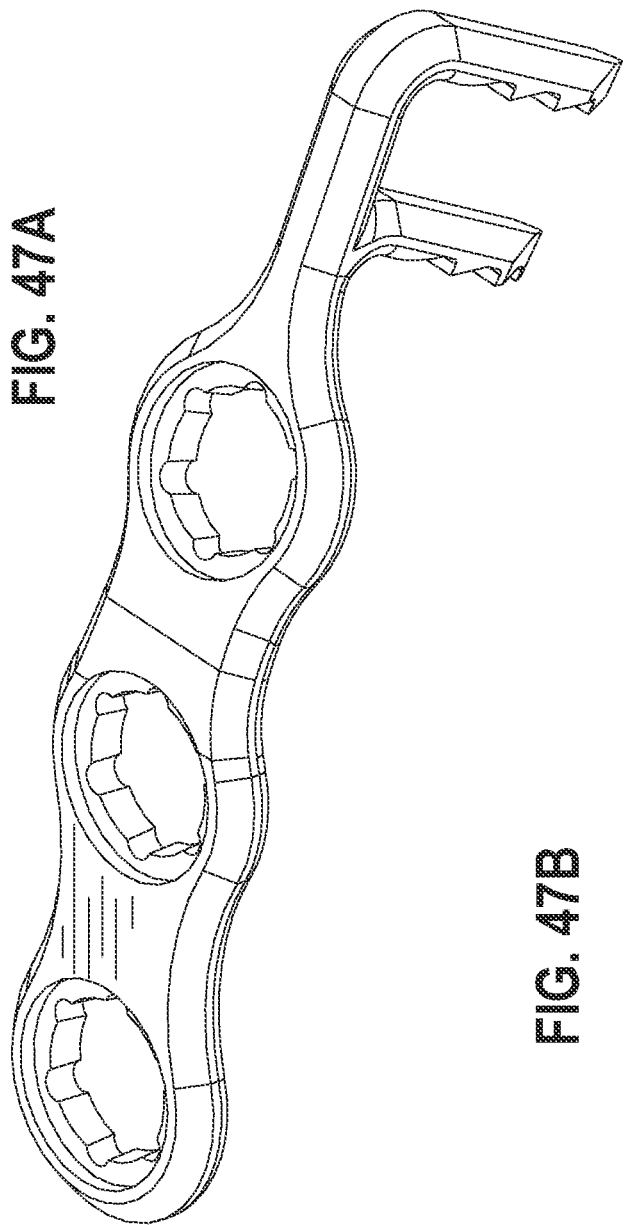
FIG. 47A is a perspective view and FIG. 47B is a side elevation view of a twenty-fifth embodiment of a plate having a pair of legs depending from a linear extension and arranged in-line and two in-line screw holes in an inclined end portion of the body at an opposite end of the extension from the legs, the pair of legs each being at an acute angle relative to the extension, and an intermediate third screw hole in the body between the extension and the other inclined end portion of the body.
Figure 47B:
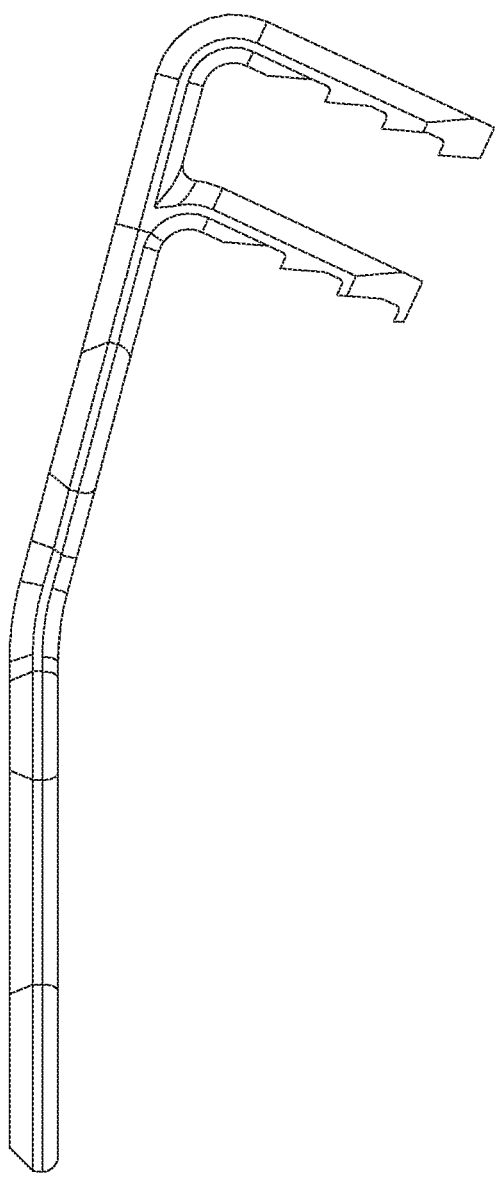

FIGS. 42A and 42B show a twentieth embodiment of a plate having a body portion with a pair of legs at one thereof and two offset screw holes in an inclined end portion of the body, the pair of legs being at an acute angle relative to the body. Optionally, an intermediate third screw hole can be formed in the body between the legs and the inclined end portion of the body, as in the twenty-first embodiment of a plate shown in FIGS. 43A and 43B.

FIGS. 44A and 44B show a twenty-second embodiment of a plate having a body portion with a pair of legs at one thereof and two in-line screw holes in an inclined end portion of the body, the pair of legs being at an acute angle relative to the body. Optionally, an intermediate third screw hole is provided in the body between the legs and the inclined end portion of the body, as in the twenty-third embodiment of the plate shown in FIGS. 45A and 45B.

FIGS. 46A and 46B show a twenty-fourth embodiment of a plate having a pair of legs depending from a linear extension and arranged in-line and two in-line screw holes in an inclined end portion of the body at an opposite end of the extension from the legs, the pair of legs each being at an acute angle relative to the extension. Optionally, an intermediate third screw hole is provided in the body between the extension and the other inclined end portion of the body, as in the twenty-fifth embodiment of a plate shown in FIGS. 47A and 47B.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

The invention claimed is:

1. A plate insertion tool for use with a compression plate having a body portion with one or more apertures each for receiving a screw and a pair of legs at one end that are each connected to the body at an acute angle and spaced apart by a shoulder, the plate insertion tool being usable to temporarily tension the legs prior to insertion into holes in a bone, the plate insertion tool comprising:
a pair of facing, inwardly extending fingers being movable between a clamping position for clamping therebetween, in use, the legs of the compression plate, and an open position where, in use, the inwardly extending fingers are spaced from the legs of the compression plate, the pair of inwardly extending fingers being closer to each other in the clamping position as compared to the open position;
a pushing finger movable between a retracted position and an extended position relative to the pair of inwardly extending fingers and having an engagement portion defining a distal end positioned for engaging, in use, the shoulder of the compression plate such that when the pushing finger moves to the extended position the legs are temporarily tensioned by bending the legs away from the body; and
a handle, having a longitudinal axis a proximal end, for moving the pushing finger between the retracted position and the extended position, the pair of inwardly extending fingers being closer to the proximal end of the handle than the distal end of the pushing finger, along the longitudinal axis of the handle when the pushing finger is in the extended position.

2. The plate insertion tool of claim 1, further comprising a rotatable handle, wherein the pusher finger is movable between the retracted position and the extended position relative to the handle upon rotation of the handle.

3. The plate insertion tool of claim 2, wherein the handle has an axis of rotation coinciding with the longitudinal axis and wherein the pair of inwardly extending fingers are fixed in an axial direction relative to the axis of rotation of the handle.

4. The plate insertion tool of claim 3, wherein the pair of inwardly extending fingers are closer to the axis of rotation of the handle in the clamping position as compared to the open position.

5. The plate insertion tool of claim 1, wherein the pair of inwardly extending fingers are closer to the proximal end of the handle than the distal end of the pushing finger when the pushing finger is in the retracted position.

6. A plate insertion tool for use with a compression plate having a body portion with one or more apertures each for receiving a screw and a pair of legs at one end that are each connected to the body at an acute angle and spaced apart by a shoulder, the plate insertion tool being usable to temporarily tension the legs prior to insertion into holes in a bone, the plate insertion tool comprising:
a pair of facing, inwardly extending fingers being movable between a clamping position for clamping therebetween, in use, the legs of the compression plate, and an open position where, in use, the inwardly extending fingers are spaced from the legs of the compression plate, the pair of inwardly extending fingers being closer to each other in the clamping position as compared to the open position; and
a pushing finger movable between a retracted position and an extended position relative to the pair of inwardly extending fingers and positioned for engaging, in use, the shoulder of the compression plate such that when the pushing finger moves to the extended position the legs are temporarily tensioned by bending the legs away from the body;
further comprising a rotatable handle, wherein the pusher finger is movable between the retracted position and the extended position relative to the handle upon rotation of the handle;
wherein the handle has an axis of rotation and wherein the pair of inwardly extending fingers are fixed in an axial direction relative to the axis of rotation of the handle; and
wherein the pair of inwardly extending fingers are closer to the axis of rotation of the handle in the clamping position as compared to the open position;
a head fixed in an axial direction relative to the handle, the head having a bottom surface for abutting, in use, a top surface of the body of the compression plate; and
a first arm having one of the pair of inwardly extending fingers and a second arm having the other of the pair of inwardly extending fingers, the first and second arms being slidably mounted relative to the head for sliding relative to each other and the head between the clamping position and the open position, the pair of inwardly extending fingers being disposed adjacent to and spaced from the bottom surface of the head when in the clamping position.

7. The plate insertion tool of claim 6, wherein:
the first arm has a first arm actuator at an end portion thereof opposite the one of the pair of inwardly extending fingers;
the second arm has a second arm actuator at an end portion thereof opposite the other of the pair of inwardly extending fingers;
the first arm actuator and the other of the pair of inwardly extending fingers being disposed on one side of the pusher finger and the second arm actuator and the other of the one of the pair of inwardly extending fingers being disposed on an opposite side of the pusher finger; and
a spring disposed between the first arm actuator and the second arm actuator to push the first arm actuator and the second arm actuator away from each other, thereby moving the pair of inwardly extending fingers from the open position toward the clamping position.

8. The plate insertion tool of claim 6, wherein the pusher finger is mounted relative to a threaded shaft passing through an opening in the head and into a threaded bore of the handle, the opening and the shaft being shaped to restrict rotation of the shaft and pusher finger, rotation of the handle causing the threaded shaft to advance and retract relative to the head.

9. A system for joining bones together, the system comprising:
a compression plate having a body portion with one or more apertures each for receiving a bone screw and a pair of legs at one end that are each connected to the body at an acute angle and spaced apart by a shoulder; and
a plate insertion tool comprising:
a pair of facing, inwardly extending fingers being movable between a clamping position for clamping therebetween, in use, the legs of the compression plate, and an open position where, in use, the inwardly extending fingers are spaced from the legs of the compression plate, the pair of inwardly extending fingers being closer to each other in the clamping position as compared to the open position; and
a pushing finger movable between a retracted position and an extended position relative to the pair of inwardly extending fingers and positioned for engaging, in use, the shoulder of the compression plate such that when the pushing finger moves to the extended position the legs are temporarily tensioned by bending the legs away from the body.

10. A method of using the system of claim 9, the method comprising:
drilling a pair of guide holes for receiving the legs of the compression plate;

clamping the compression plate relative to the plate insertion tool by moving the pair of inwardly extending fingers from the open position to the clamping position;

engaging the shoulder of the compression plate with the pusher finger;

moving the pusher finger toward the extended position to temporality tension the legs by pivoting the legs away from the body of the compression plate to a greater angle relative to the body as compared to the acute angle; and inserting the legs of the compression plate into the guide holes when the legs are pivoted away from the body to the greater angle.

11. The method of claim 10, further comprising, after the step of inserting the legs of the compression plate into the guide holes when the legs are pivoted away from the body to the greater angle, inserting a bone screw through one of the one or more apertures of the body of the compression plate and into a pre-drilled guide hole.

12. The method of claim 11, further comprising, after the step of inserting a bone screw through one of the one or more apertures of the body of the compression plate and into a pre-drilled guide hole:

disengaging the pusher finger from the shoulder of the compression plate by moving the pusher finger toward the retracted position; and unclamping the compression plate relative to the plate insertion tool by moving the pair of inwardly extending fingers toward the open position.

13. The method of claim 11, further comprising, after the step of inserting the legs of the compression plate into the guide holes when the legs are pivoted away from the body to the greater angle and before the step of inserting a bone screw through one of the one or more apertures of the body of the compression plate and into a pre-drilled guide hole, tensioning the body of the compression plate by pulling the body of compression plate in a direction generally away from the legs thereof.

14. The method of claim 13, wherein the system includes a tensioning tool having a pair of handles that can be squeezed toward each other to move operative ends of the handles toward each other, one of the operative ends having means for temporarily connecting to the compression plate and another of the operative ends have means for temporarily being fixed relative to the bone, the step of tensioning the body of the compression plate further comprising:

temporarily connecting the one of the operative ends to the compression plate;

temporarily fixing the another of the operative ends to the bone;

squeezing the handles toward each other to pull the operative ends toward each other to pull the body of compression plate in a direction generally away from the legs thereof.

15. The method of claim 14, further comprising, after the step of inserting a bone screw through one of the one or more apertures of the body of the compression plate and into a pre-drilled guide hole:

disengaging the pusher finger from the shoulder of the compression plate by moving the pusher finger toward the retracted position; and unclamping the compression plate relative to the plate insertion tool by moving the pair of inwardly extending fingers toward the open position.

16. A method of joining bones together using a compression plate having a body portion with one or more apertures each for receiving a bone screw and a pair of legs at one end that are each connected to the body at an acute angle and spaced apart by a shoulder, the method comprising:

providing the compression plate;

drilling a pair of guide holes in one of the bones for receiving the legs of the compression plate;

pushing the shoulder of the compression plate away from the legs while holding the legs to temporarily tension the legs by pivoting the legs away from the body of the compression plate to a greater angle relative to the body as compared to the acute angle; and inserting the legs of the compression plate into the guide holes when the legs are pivoted away from the body to the greater angle.

17. The method of claim 16, further comprising, after the step of inserting the legs of the compression plate into the guide holes when the legs are pivoted away from the body to the greater angle, inserting a bone screw through one of the one or more apertures of the body of the compression plate and into a pre-drilled guide hole.

18. The method of claim 17, further comprising, after the step of inserting a bone screw through one of the one or more apertures of the body of the compression plate and into a pre-drilled guide hole, stopping pushing the shoulder of the compression plate away from the legs.

19. The method of claim 17, further comprising, after the step of inserting the legs of the compression plate into the guide holes when the legs are pivoted away from the body to the greater angle and before the step of inserting a bone screw through one of the one or more apertures of the body of the compression plate and into a pre-drilled guide hole, tensioning the body of the compression plate by pulling the body of compression plate in a direction generally away from the legs thereof.

* * * * *